United States Patent
Li et al.

(10) Patent No.: US 12,100,518 B2
(45) Date of Patent: Sep. 24, 2024

(54) GENERATING ONTOLOGY BASED ON BIOMARKERS

(71) Applicant: International Business Machines Corporation, Armonk, NY (US)

(72) Inventors: Ying Li, Fort Lee, NJ (US); Mohamed Ghalwash, Yorktown Heights, NY (US); Kenney Ng, Arlington, MA (US); Vibha Anand, Cambridge, MA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 517 days.

(21) Appl. No.: 17/377,725

(22) Filed: Jul. 16, 2021

(65) Prior Publication Data

US 2023/0043676 A1    Feb. 9, 2023

(51) Int. Cl.
*G16H 50/70*    (2018.01)
*G06F 40/30*    (2020.01)
(Continued)

(52) U.S. Cl.
CPC .............. *G16H 50/70* (2018.01); *G06F 40/30* (2020.01); *G16H 10/40* (2018.01); *G16H 10/60* (2018.01);
(Continued)

(58) Field of Classification Search
CPC ........ G16H 50/70; G16H 10/40; G16H 10/60; G16H 50/20; G16H 50/30; G16H 70/60; G16H 50/50; G16H 40/67; G06F 40/30
See application file for complete search history.

(56) References Cited

U.S. PATENT DOCUMENTS

| 8,015,136 B1 | 9/2011 | Baker et al. |
| 9,238,841 B2 | 1/2016 | Wong et al. |

(Continued)

OTHER PUBLICATIONS

Lyappan, A., Kawalia, S.B., Raschka, T et al. NeuroRDF: semantic integration of highly curated data to prioritize biomarker candidates in Alzheimer's disease. J Biomed Semant 7, 45 (2016). https://doi.org/10.1186/s13326-016-0079-8 (Year: 2016).*

(Continued)

*Primary Examiner* — Eliza A Lam
(74) *Attorney, Agent, or Firm* — Amin, Turocy & Watson, LLP

(57) ABSTRACT

Techniques for generating an ontology based on biomarker information associated with persons to facilitate improving clinical predictions relating to medical conditions are presented. An ontology generator component (OGC) can extract clinical features associated with patients and their associated times from medical records or databases to develop clinical profiles associated with the patients and relating to a medical condition. OGC can develop an ontology relating to the medical condition, including progression and severity of biomarkers associated with the medical condition, based on the clinical profiles and domain knowledge information relating to the medical condition. OGC can determine global features relating to progression and severity associated with the medical condition based on the ontology. At a forecasting point, the global features can be extracted from the ontology and applied to a prediction model to enhance prediction of onset of, or progression of, the medical condition for a patient.

20 Claims, 9 Drawing Sheets

(51) Int. Cl.
  *G16H 10/40* (2018.01)
  *G16H 10/60* (2018.01)
  *G16H 50/20* (2018.01)
  *G16H 50/30* (2018.01)
  *G16H 50/50* (2018.01)
  *G16H 70/60* (2018.01)
(52) U.S. Cl.
  CPC ............. *G16H 50/20* (2018.01); *G16H 50/30* (2018.01); *G16H 70/60* (2018.01); *G16H 50/50* (2018.01)

(56) References Cited

U.S. PATENT DOCUMENTS

| | | |
|---|---|---|
| 2009/0144089 A1 | 6/2009 | Heywood et al. |
| 2014/0350954 A1 | 11/2014 | Ellis et al. |
| 2017/0091422 A1 | 3/2017 | Kumar et al. |
| 2020/0176098 A1* | 6/2020 | Lucas ................ G16H 10/60 |
| 2020/0279620 A1* | 9/2020 | Bassett, Jr. ............ G16B 50/30 |

OTHER PUBLICATIONS

P.C., Sherimon et al., "Ontology Based System Architecture to Predict the Risk of Hypertension in Related Diseases," International Journal of Information Processing and Management (IJIPM), vol. 4, No. 4, Jun. 2013, 7 pages.
Li et al., "Predicting Type 1 Diabetes Onset using Novel Survival Analysis with Biomarker Ontology," AMIA Annu Symp Proc. Jan. 25, 2021;2020:727-736.
Jonsdottir et al., "Childhood thyroid autoimmunity and relation to islet autoantibodies in children at risk for type 1 diabetes in the diabetes prediction in skane (DiPiS) study," Autoimmunity. 2018;51(5):228-237.
Veijola et al., "Dysregulation of glucose metabolism in preclinical type 1 diabetes," Pediatric diabetes. 2016;17:25-30.
Erlich et al., "HLA DR-DQ haplotypes and genotypes and type 1 diabetes risk: analysis of the type 1 diabetes genetics consortium families," Diabetes. Apr. 2008 ; 57(4), 23 pages.
Siljander et al., "Predictive characteristics of diabetes-associated autoantibodies among children with HLA-conferred disease susceptibility in the general population," Diabetes. 2009;58(12):2835-2842.
Raykar et al., "On Ranking in Survival Analysis: Bounds on the Concordance Index," Advances in neural information processing systems, Advances in Neural Information Processing Systems 20 (NIPS 2007), 9 pages.
Harrell et al., "Multivariable prognostic models: issues in developing models, evaluating assumptions and adequacy, and measuring and reducing errors," Statistics in medicine. 1996;15(4):361-387.
Cox, "Regression models and life-tables," Journal of the Royal Statistical Society. Series B (Methodological), vol. 34, No. 2 (1972), pp. 187-220.
Mittal et al., "Large-Scale Parametric Survival Analysis," Stat Med. Oct. 15, 2013; 32(23), 27 pages.
Sosenko et al., "The prediction of type 1 diabetes by multiple autoantibody levels and their incorporation into an autoantibody risk score in relatives of type 1 diabetic patients," Diabetes Care, vol. 36, Sep. 2013, 6 pages.
Liu et al., "1690-P: Predicting Onset of Type 1 Diabetes Using a Novel Interaction Model," Diabetes Jun. 2019; 68 (Supplement 1), 5 pages.
Wang et al., "Should Health Care Demand Interpretable Artificial Intelligence or Accept "Black Box" Medicine?," Annals of Internal Medicine. 2020;172:59-60.
Kohler et al., "Flexible Bayesian additive joint models with an application to type 1 diabetes research," arXiv:1611.01485v2 [stat. ME] Jan. 20, 2017, 25 pages.

Xu et al., "Prognostic accuracy of immunologic and metabolic markers for type 1 diabetes in a high-risk population: receiver operating characteristic analysis," Diabetes Care. Oct. 2012; 35(10):1975-80.
Zhang, "Domain ontology development of knowledge base in cardiovascular personalized health management," Antai College of Economics & Management Shanghai JiaoTong University, 2015, 27 pages.
Zhang et al., "Domain ontology development of knowledge base in cardiovascular personalized health management," Journal of Management Analytics 6.4 (2019), 37 pages.
Bouamrane et al., "Development of an ontology for a preoperative risk assessment clinical decision support system." 2009 22nd IEEE International Symposium on Computer-Based Medical Systems. IEEE, 2009, 6 pages.
Garg et al., "Effects of computerized clinical decision support systems on practitioner performance and patient butcomes: a systematic review." Jama 293.10 (2005), 16 pages.
Tacylildiz et al., "A decision support system on the obesity management and consultation during childhood and adolescence using ontology and semantic rules." Journal of Biomedical Informatics 110 (2020): 103554, 18 pages.
Lykouentzou et al., "Ontology-based operational risk management." 2011 IEEE 13th Conference on Commerce and Enterprise Computing. IEEE, 2011, 8 pages.
Abbas et al. "Personalized healthcare cloud services for disease risk assessment and wellness management using social media." Pervasive and Mobile Computing 28 (2015), 19 pages.
Wang et al., "Multiple Biomarkers for the Prediction of First Major Cardiovascular Events and Death," N Engl J Med 2006; 355:2631-2639.
"Clinical Classifications Software (CCS) for ICD-10-PCS (beta version)," Agency for Healthcare Research and Quality, https://www.hcup-us.ahrq.gov/toolssoftware/ccs10/ccs10.jsp, last modified Nov. 5, 2019, 4 pages.
Haug et al., "An ontology-driven, diagnostic modeling system," Journal of the American Medical Informatics Association, vol. 20, Issue e1, Jun. 2013, 9 pages.
Tao et al., "CNTRO 2.0: A Harmonized Semantic Web Ontology for Temporal Relation Inferencing in Clinical Narratives," AMIA Jt Summits Transl Sci Proc. 2011; Published online Mar. 7, 2011, 5 pages.
Bouwens et al., "Temporal Patterns of 14 Blood Biomarker candidates of Cardiac Remodeling in Relation to Prognosis of Patients With Chronic Heart Failure-The Bio- SH i FT Study," J Am Heart Assoc. Feb. 19, 2019;8(4):e009555, 20 pages.
"Time Ontology in OWL—W3C Candidate Recommendation Mar. 26, 2020," https://www.w3.org/TR/owl-time/, accessed Jul. 7, 2021, 49 pages.
Insel et al., "Staging Presymptomatic Type 1 Diabetes: A Scientific Statement of JDRF, the Endocrine Society, and the American Diabetes Association," Diabetes Care vol. 38, Oct. 2015, 11 pages.
Bingley et al., "Prediction of IDDM in the General Population: Strategies Based on Combinations of Autoantibody Markers," Diabetes Nov. 1997; 46(11): 1701-1710.
Ziegler et al., "Seroconversion to Multiple Islet Autoantibodies and Risk of Progression to Diabetes in Children," Jun. 2013, JAMA—The Journal of the American Medical Association 309(23):2473-9.
Orban et al., "Pancreatic islet autoantibodies as predictors of type 1 diabetes in the Diabetes Prevention Trial-Type 1," Diabetes Care 32:2269-2274, 2009, 6 pages.
Steck et al., "Predictors of Progression From the Appearance of Islet Autoantibodies to Early Childhood Diabetes: The Environmental Determinants of Diabetes in the Young (TEDDY)," Diabetes Care vol. 38, May 2015, 6 pages.
Herold et al., "An Anti-CD3 Antibody, Teplizumab, in Relatives at Risk for Type 1 Diabetes," N Engl J Med. 2019 15;381(7):603-13.
Ziegler et al., "Yield of a Public Health Screening of Children for Islet Autoantibodies in Bavaria, Germany," JAMA, Jan. 28, 2020;323(4):339-51.
McQueen et al., "Cost and Cost-effectiveness of Large-scale Screening for Type 1 Diabetes in Colorado," Diabetes Care 2020;43:1496-1503.

(56) References Cited

OTHER PUBLICATIONS

Spencer et al., "Fluctuating islet-cell autoimmunity in unaffected relatives of patients with insulin-dependent diabetes," Lancet. Apr. 7, 1984;1(8380):764-6.
Kimpimaki et al., "Natural history of beta-cell autoimmunity in young children with increased genetic susceptibility to type 1 diabetes recruited from the general population," J Clin Endocrinol Metab. Oct. 2002; 87(10):4572-9.
Vehik et al., "Reversion of b-Cell Autoimmunity Changes Risk of Type 1 Diabetes: TEDDY Study," Diabetes Care vol. 39, Sep. 2016, 8 pages.
Anand et al., "1345-P: Presymptomatic and Clinical T1D in The U.S., Sweden, and Finland: Joint Analysis of Four Birth Cohort Studies," Diabetes. Jun. 2019;68(Supplement 1):1345-P, 6 pages.
Kupila et al., "Feasibility of genetic and immunological prediction of Type I diabetes in a population-based birth cohort," Diabetologia. Mar. 2001;44(3):290-7.
Ziegler et al., "Autoantibody appearance and risk for development of childhood diabetes in offspring of parents with type 1 diabetes: the 2-year analysis of the German BABYDIAB Study," Diabetes. Mar. 1999;48(3):460-8.
Larsson et al., "A Swedish approach to the prevention of type 1 diabetes," Pediatric Diabetes. Jul. 1, 2016;17(S22):73-7.
Rewers et al., "Newborn screening for HLA markers associated with IDDM: diabetes autoimmunity study in the young (DAISY)," Diabetologia. Jul. 1996;39(7):807-12.
Wion et al., "Population-wide infant screening for HLA-based type 1 diabetes risk via dried blood spots from the public health infrastructure," Ann N Y Acad Sci. Nov. 2003;1005:400-3.
"Diagnosis and Classification of Diabetes Mellitus," American Diabetes Association, Diabetes Care vol. 37, Supplement 1, Jan. 2014, 10 pages.
Vock et al., "Adapting machine learning techniques to censored time-to-event health record data: A general-purpose approach using inverse probability of censoring weighting," Journal of Biomedical Informatics. Jun. 2016;61, 34 pages.
Endesfelder et al., "Time-Resolved Autoantibody Profiling Facilitates Stratification of Preclinical Type 1 Diabetes in Children," Diabetes vol. 68, Jan. 2019, 12 pages.
Kohler et al., "Joint modeling of longitudinal autoantibody patterns and progression to type 1 diabetes: results from the TEDDY study," Acta Diabetol. Nov. 2017 ; 54(11), 20 pages.
Hagopian et al., "The Environmental Determinants of Diabetes in the Young (TEDDY): genetic criteria and International diabetes risk screening of 421,000 infants," Pediatr Diabetes. Dec. 2011 ; 12(8), 15 pages.
Regnell et al., "Early prediction of autoimmune (type 1) diabetes," Diabetologia (2017) 60:1370-1381.
Ziegler et al., "Why is the presence of autoantibodies against GAD associated with a relatively slow progression to clinical diabetes?," Diabetologia (2020) 63:1665-1666.
Jacobsen et al., "Predicting progression to type 1 diabetes from ages 3 to 6 in islet autoantibody positive TEDDY children," Pediatr Diabetes. May 2019 ; 20(3), 16 pages.
Bingley et al., "Diabetes Antibody Standardization Program: First Assay Proficiency Evaluation," Diabetes May 2003; 52(5): 1128-1136.
Lampasona et al., "Islet Autoantibody Standardization Program 2018 Workshop: Interlaboratory Comparison of Glutamic Acid Decarboxylase Autoantibody Assay Performance," Clinical Chemistry. Sep. 1, 2019;65(9):1141-52.
Maahs et al., "Epidemiology of Type 1 Diabetes," Endocrinol Metab Clin North Am. Sep. 2010 ; 39(3): 481-497.
Liu et al., "Early Prediction of Diabetes Complications from Electronic Health Records: A Multi-Task Survival Analysis Approach," In: Thirty-Second AAAI Conference on Artificial Intelligence; 2018, 8 pages.
Pihoker et al., "Autoantibodies in Diabetes," Diabetes Dec. 2005; 54(suppl 2): S52-S61, 10 pages.
Michels et al., "Prediction and prevention of type 1 diabetes: update on success of prediction and struggles at prevention," Pediatr Diabetes. Nov. 2015 ; 16(7), 33 pages.
Steck et al., "Age of islet autoantibody appearance and mean levels of insulin, but not GAD or IA-2 autoantibodies, predict age of diagnosis of type 1 diabetes: diabetes autoimmunity study in the young," Diabetes care. 2011;34(6): 1397-1399.
Morran et al., "Immunogenetics of Type 1 Diabetes Mellitus," Mol Aspects Med. Apr. 2015 ; 42: 42-60.
Lambert et al., "Absolute risk of childhood-onset type 1 diabetes defined by human leukocyte antigen class II genotype: a population-based study in the United Kingdom," The Journal of Clinical Endocrinology & Metabolism 89(8):4037-4043, 2004.
Ziegler et al., "Prediction and Pathogenesis in Type 1 Diabetes," Immunity. Apr. 23, 2010; 32(4), 21 pages.
Patterson et al., "Incidence trends for childhood type 1 diabetes in Europe during 1989-2003 and predicted new cases 2005-20: a multicentre prospective registration study," The Lancet. 2009;373(9680):2027-2033.
Bonifacio, "Predicting type 1 diabetes using biomarkers," Diabetes Care Jun. 2015; 38(6): 989-996.
Haug et al., "An ontology-driven, diagnostic modeling system," Journal of the American Medical Informatics Association, 2013;20:e102-e110.

* cited by examiner

GENERATING ONTOLOGY BASED ON BIOMARKERS

BACKGROUND

The subject disclosure relates to computer-related analysis, and more specifically, to generating an ontology based on biomarker information relating to biomarkers.

SUMMARY

The following presents a summary to provide a basic understanding of one or more embodiments of the disclosed subject matter. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, devices, structures, computer-implemented methods, apparatuses, and/or computer program products that can facilitate determining and/or generating an ontology relating to a medical condition based on medical data.

According to an embodiment, a computer-implemented method comprises determining, by a system operatively coupled to a processor, an ontology relating to a medical condition and medical statuses associated with a group of persons with regard to the medical condition based on analyzing temporal medical data associated with the group of persons and domain knowledge data relating to the medical condition. The computer-implemented method also comprises: based on the ontology, at a defined time, determining, by the system, a group of global temporal features relating to a person and a level of severity associated with the medical condition that facilitates a prediction of a future medical status relating to the medical condition and associated with the person.

Another embodiment relates to a system comprising a memory that stores computer-executable components; and a processor, operatively coupled to the memory, that executes computer-executable components. The computer-executable components can comprise an ontology generator component that generates an ontology relating to a disease and medical statuses associated with a group of patients in connection with the disease based on an analysis temporal clinical data associated with the group of patients and domain knowledge data relating to the disease. The computer-executable components also can include a feature extractor component that, at an index time, extracts a group of global temporal features relating to a patient and a severity level associated with the disease, wherein the group of global temporal features facilitates a prediction of a future medical status relating to the disease and associated with the patient.

A further embodiment relates to a computer program product that facilitates determining an ontology, the computer program product comprising a computer readable storage medium having program instructions embodied therewith. The program instructions can be executable by a processor to cause the processor to determine the ontology relating to a medical condition and medical statuses associated with a group of patients with regard to the medical condition based on analyzing temporal medical data associated with the group of patients and domain knowledge information relating to the medical condition. The program instructions also can be executable by the processor to: based on the ontology, at a prediction time, determine a group of global temporal features relating to a patient and a level of severity associated with the medical condition that facilitates a prediction of a future medical status relating to the medical condition and associated with the patient.

These and other features will become apparent from the following detailed description of illustrative embodiments thereof, which is to be read in connection with the accompanying drawings.

DETAILED DESCRIPTION

Figure 1:
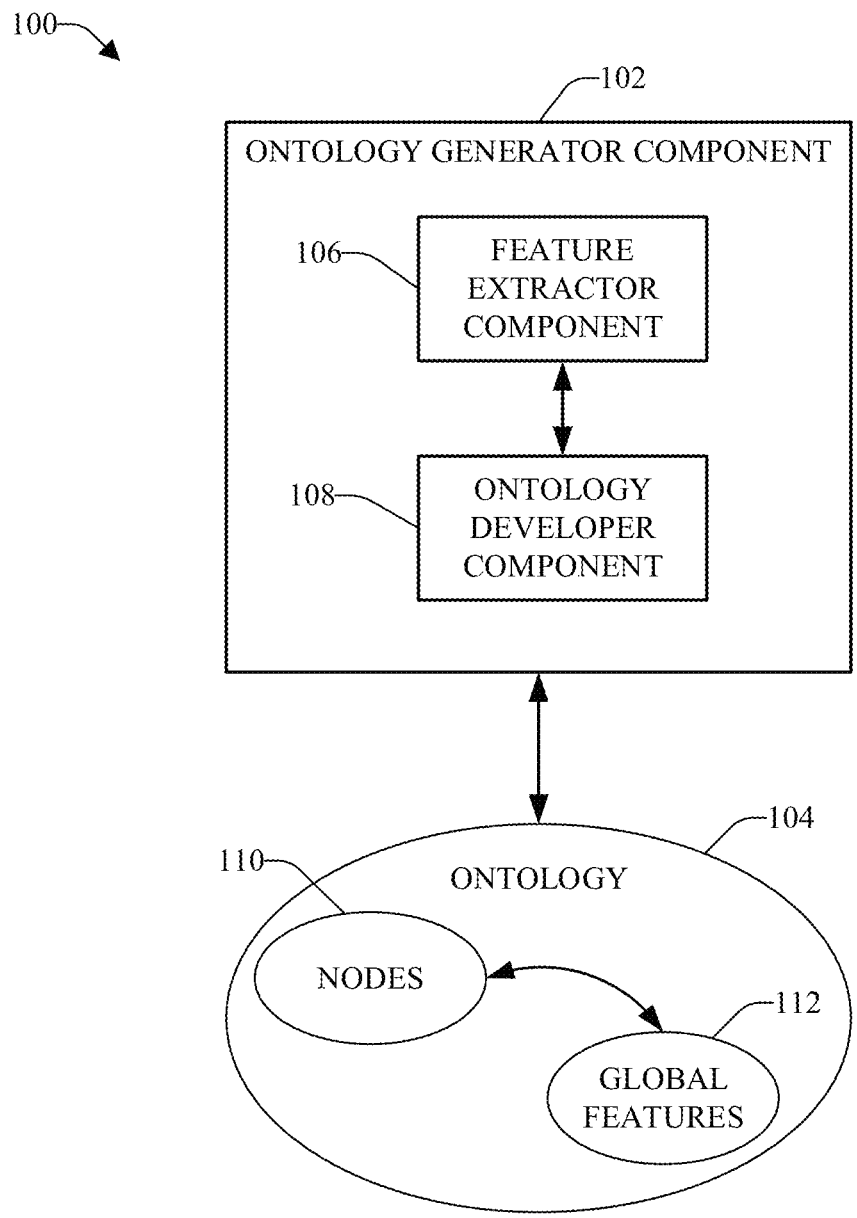
FIG. 1 illustrates a block diagram of an example, non-limiting system that can determine and generate ontologies based on clinical features, comprising biomarkers, associated with persons to facilitate enhancing clinical predictions relating to diseases or other medical conditions, in accordance with various aspects and embodiments of the disclosed subject matter.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Many people can benefit from assessing their risk for potentially being inflicted with one or more diseases or medical conditions. Also, people with an existing disease or medical condition can benefit from assessing more accurately the progression of their existing disease or medical condition.

Certain blood sample-based biomarkers (e.g., creatinine, cholesterol, or other biomarkers) are known to have a practical advantage of being associated with development of their related diseases. The use of these biomarkers derived from a single time point (e.g., such as at the time of an encounter with a physician during a physician office visit) may not be sufficiently accurate for the effective prediction of onset of a disease. Existing techniques that consider progression of autoantibodies to predict disease onset can be deficient, as, for example, such existing techniques can be inaccurate or of limited accuracy.

To that end, the various embodiments herein relate to techniques for determining and generating an ontology based on biomarker information associated with persons (e.g., patients) to facilitate enhancing clinical predictions relating to diseases or other medical conditions. An ontology generator component can analyze medical records associated with a group of persons, wherein the medical records can comprise medical data relating to a medical condition (e.g., a disease or other medical condition). Based at least in part on the results of such analysis of the medical records, the ontology generator component can extract clinical features, including the times (e.g., time of laboratory (lab) testing, or time of collection of medical data, such as sensor data) associated with the clinical features, associated with persons of the group of persons, and can develop clinical profiles associated with the persons and relating to the medical condition. The clinical features can comprise biomarker information relating to biomarkers associated with the medical condition and associated with the persons of the group of persons. The ontology generator component also can receive domain knowledge information relating to the medical condition from a group of medical experts with knowledge regarding the medical condition.

The ontology generator component can determine and/or develop an ontology relating to the medical condition, including progression (e.g., temporal progression) and severity of the biomarkers associated with the medical condition, based on clinical profile data of the clinical profiles, comprising the clinical features, and the domain knowledge information relating to the medical condition. The ontology generator component can determine global features relating to progression and severity associated with the medical condition based on the ontology. The global features can comprise, for example, a highest risk so far of onset of the medical condition by a person, a pathway length to the highest risk so far of the onset of the medical condition by the person, or another desired global feature.

In some embodiments, at a desired forecasting point (e.g., prediction point or index time), the ontology generator component can extract the global features from the ontology and can apply or facilitate applying the global features and/or the other features relating to the medical condition to a prediction model to predict an onset of the medical condition for a person (e.g. patient), or a progression of, the medical condition for a person who already has the medical condition. The prediction relating to the onset of, or the progression of, the medical condition for the person can be enhanced (e.g., improved or optimized) due in part to the ontology, as compared to existing techniques for predicting on of a medical condition for a person or progression of the medical condition in a person who already has the medical condition.

These and other aspects and embodiments of the disclosed subject matter will now be described with respect to the drawings.

FIG. 1 illustrates a block diagram of an example, non-limiting system 100 that can determine and generate ontologies based on clinical features, comprising biomarkers, associated with persons (e.g., patients) to facilitate enhancing clinical predictions relating to diseases or other medical conditions, in accordance with various aspects and embodiments of the disclosed subject matter. The system 100 can comprise an ontology generator component 102 that can comprise various components, and can determine, develop, and/or generate ontologies, such as ontology 104, based on clinical features, comprising biomarkers, associated with persons (e.g., patients) to facilitate enhancing clinical predictions relating to diseases or other medical conditions. For instance, the ontology generator component 102 can determine, develop, and/or generate a different ontology 104 for each desired type of medical condition.

The ontology generator component 102 can receive medical data associated with a group of persons (e.g., patients) from one or more data sources, in connection with a medical condition (e.g., disease or other type of medical condition). The one or more data sources can comprise, for example, one or more databases that contain electronic health records of persons, one or more disease registries that contain medical data regarding persons and diseases or disease statuses, and/or another data source that contains medical data. The medical data can comprise various types of health, medical, and/or other information relating to each person of the group of persons.

The ontology generator component 102 can comprise a feature extractor component 106 that can analyze the medical data associated with the group of persons. Based at least in part on the results of the analysis of the medical data, the feature extractor component 106 can determine and generate a group of clinical profiles, comprising clinical features, associated with the group of persons. As part of the analysis of the medical data, the feature extractor component 106 can identify and extract various types of clinical features associated with each person. For instance, with regard to each person of the group of persons, the feature extractor component 106 can identify and extract clinical features comprising lab test information (e.g., lab test results), biomarker information relating to various biomarkers associated with the medical condition, commodities information (e.g., sensor data or other health or medical data relating to one or more commodities, such as one or more medical or health sensors or other medical devices, utilized to monitor the health status of the person), medications (e.g., medications prescribed for or taken by a person), and/or other clinical (e.g., medical or health) information relating to the person and/or medical condition. With regard to the medical condition, the feature extractor component 106 can generate respective clinical profiles, comprising respective clinical features, of respective persons of the group of persons. A clinical profile associated with a person can comprise, for example, information regarding lab test results, biomarker information relating to a group of biomarkers associated with the medical condition, health or medical information associated with one or more commodities (e.g., sensors or other medical devices) relating to the medical condition, medications relating to the medical condition, or other clinical information relating to the medical condition, associated with the person.

In some embodiments, with regard to the medical condition (e.g., for each desired type of medical condition), the ontology generator component 102 also can receive domain knowledge information relating to the medical condition from one or more domain knowledge sources. The one or more domain knowledge data sources can comprise one or more medical experts who have expert knowledge regarding the medical condition or one or more domain knowledge databases that contain expert domain knowledge information relating to the medical condition that has been obtained from one or more medical experts who can have expert knowledge regarding the medical condition. An individual can be a medical expert with regard to a medical condition, for example, if the individual can satisfy (e.g., meet or exceed) defined medical expert criteria relating to the medical condition.

The ontology generator component 102 can comprise an ontology developer component 108 that can determine or develop respective ontologies, such as ontology 104, relating to respective medical conditions. With regard to the medical condition (e.g., for each desired type of medical condition), the ontology developer component 108 can analyze respective clinical feature data associated with the respective clinical features of the respective persons of the group of persons and the respective times associated with the respective clinical features (e.g., as contained in the respective clinical profiles of the respective persons of the group of persons), and the domain knowledge information (e.g., expert domain knowledge) relating to the medical condition. Based on the results of such analysis, the ontology developer component 108 can determine, develop, and/or generate an ontology 104 relating to the medical condition that can consider and account for progression and severity aspects associated with the medical condition. As part of the analysis and the determining or developing of the ontology 104, the ontology developer component 108 can determine respective nodes 110 of a group of nodes where the respective nodes 110 can relate to respective statuses (e.g., medical statuses) associated with the medical condition including respective levels of progression and/or severity associated with the medical condition. In some embodiments, as part of the analysis and the determining or developing of the ontology 104, the ontology developer component 108 can determine a ranking of the respective nodes 110 and can rank the respective nodes 110 in order of the respective levels of progression and/or severity associated with the medical condition. In certain embodiments, the ontology developer component 108 can structure and rank respective nodes 110 of the ontology 104 in order of the respective levels of progression and/or severity associated with the medical condition from a lowest level of progression and/or severity associated with the medical condition to a highest level of progression and/or severity associated with the medical condition.

For instance, as part of the analysis and the determining or developing of the ontology 104 relating to the medical condition, with regard to each clinical profile (e.g., comprising clinical feature data) associated with each person of the group of persons, the ontology developer component 108 can determine the number of biomarkers (if any), and one or more types of biomarkers (if any), with regard to which the person tested positive for each clinical visit of the person, determine the number of biomarkers (if any), and one or more types of biomarkers (if any), with regard to which the person tested positive for multiple clinical visits (e.g., two or more consecutive visits) of the person, and/or determine other progression or severity related clinical features associated with the medical condition with regard to the person. Using the disclosed data-driven techniques, the ontology developer component 108 can define nodes 110 in the ontology 104 associated with the medical condition based on the respective clinical features associated with respective persons of the group of persons and the domain knowledge information relating to the medical condition, wherein respective nodes 110 can relate to respective statuses (e.g., medical condition related statuses) associated with the medical condition. For example, the ontology developer component 108 can define a node 110 or associated status as single positive biomarker (e.g., Single) when a subject (e.g., a person) is determined to have tested positive for a single biomarker relating to the medical condition. As another example, the ontology developer component 108 can define a node 110 or associated status as single type of biomarker and persistent (e.g., SinglePersistent) when a subject is determined to have tested positive for the same single biomarker relating to the medical condition in two consecutive clinical visits. As still another example, the ontology developer component 108 can define a node 110 or associated status as multiple types of positive biomarkers (e.g., Multiple or MultipleIAB) when a subject is determined to have tested positive cumulatively for more than one type of biomarker (e.g., multiple biomarkers) relating to the medical condition over clinical visits.

As yet another example, the ontology developer component 108 can define a node 110 or associated status as multiple positive biomarkers during a same visit (e.g., Multiple@SameVisit) when a subject is determined to have tested positive for more than one type of biomarker (e.g., multiple biomarkers) relating to the medical condition during a same clinical visit. As still another example, the ontology developer component 108 can define a node 110 or associated status as multiple positive biomarkers and persistent with regard to a single biomarker (e.g., MultiplePersistentOR) relating to the medical condition when a subject is determined to have tested positive for the same single biomarker relating to the medical condition during multiple clinical visits (e.g., two or more consecutive clinical visits) and tested positive for another type of biomarker during at least one of the multiple clinical visits. As yet another example, the ontology developer component 108 can define a node 110 or associated status as multiple positive biomarkers and persistent with regard to the same multiple biomarkers (e.g., MultiplePersistentAND) relating to the medical condition when a subject is determined to have tested positive for the same multiple biomarkers relating to the medical condition during multiple clinical visits (e.g., two or more consecutive clinical visits). It is to be appreciated and understood that these types of nodes 110 and statuses are non-limiting example types of nodes and statuses relating to a medical condition, and, in accordance with various aspects and embodiments, the ontology developer component 108 can determine and define other types of nodes 110 and statuses relating to a particular medical condition based on the results of analyzing clinical feature data relating to clinical features of patients and particular domain knowledge information relating to the particular medical condition.

Figure 2:
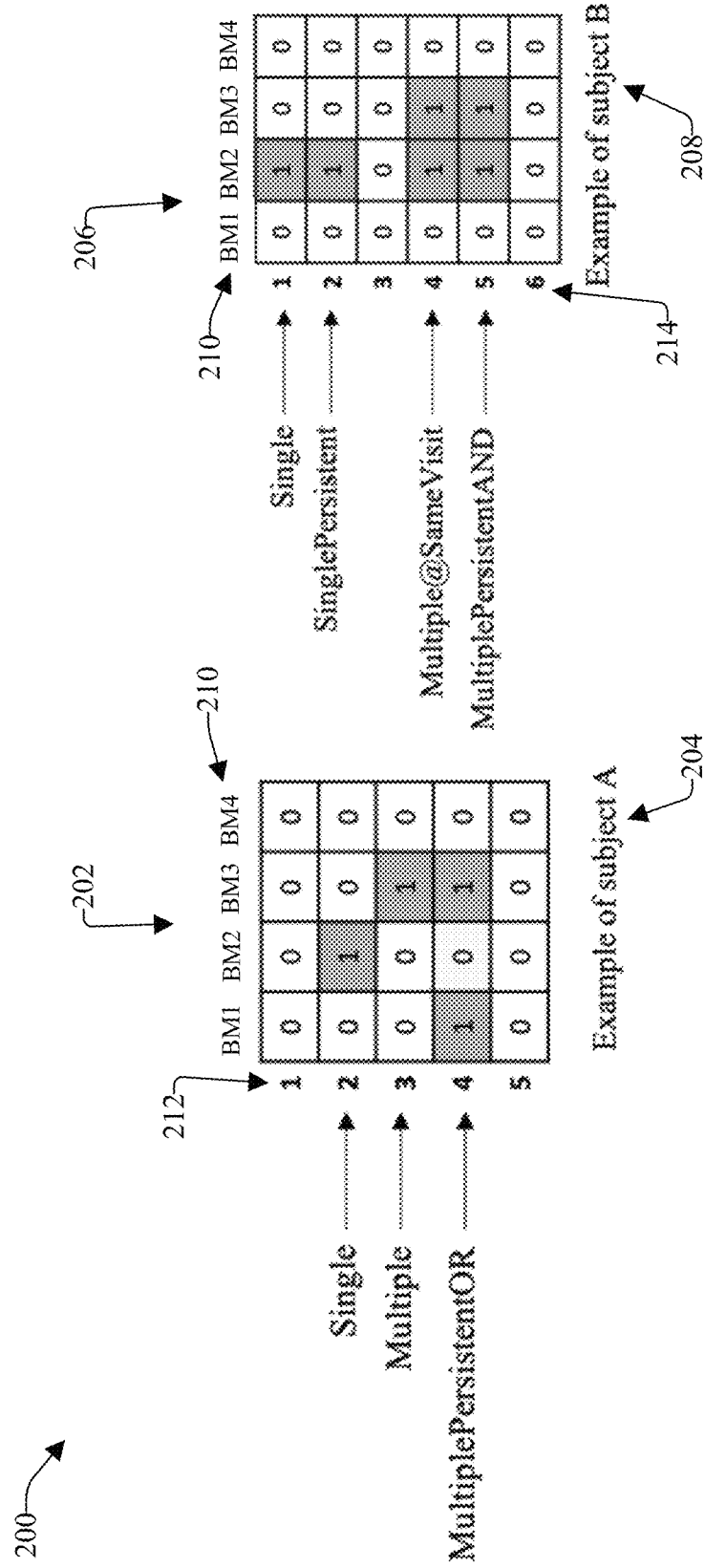
FIG. 2 depicts a diagram of example matrices relating to biomarker results of two subjects (e.g., patients) with regard to a medical condition, in accordance with various aspects and embodiments of the disclosed subject matter.

Referring to FIG. 2 (along with FIG. 1), FIG. 2 depicts a diagram of example matrices 200 relating to biomarker results of two subjects (e.g., patients) with regard to a medical condition, in accordance with various aspects and embodiments of the disclosed subject matter. The example matrices 200 can provide an illustrative explanation of the ontology that can be generated by the ontology generator component 102 as well as an example illustration of various clinical features, including medical statuses, of subjects with regard to severity and progression associated with a medical condition. These particular example matrices 200 can relate to type 1 diabetes. However, it is to be appreciated and understood that, employing the techniques of the disclosed subject matter, the ontology generator component 102 can determine and generate various types of matrices or corresponding data structures relating to various medical statuses of subjects with regard to various types of medical conditions.

The example matrices 200 can comprise matrix 202 relating to subject A 204 and matrix 206 relating to subject B 208. The ontology generator component 102 can analyze medical data relating to subject A 204 to generate a clinical profile for subject A 204, wherein the clinical profile for subject A 204 can comprise clinical profile data relating to clinical features relating to a medical condition (e.g., type 1 diabetes). The ontology generator component 102 also can determine and generate the matrix 202 relating to subject A 204 based on the clinical profile data relating to the clinical features of subject A 202 with regard to the medical condition. Similarly, the ontology generator component 102 can analyze medical data relating to subject B 208 to generate a clinical profile for subject B 208, wherein the clinical profile for subject B 208 can comprise clinical profile data relating to clinical features relating to the medical condition. The ontology generator component 102 also can determine and generate the matrix 206 relating to subject B 208 based on the clinical profile data relating to the clinical features of subject B 208 with regard to the medical condition.

The matrix 202 and matrix 206 can comprise a group of columns that can comprise information (e.g., lab rest results) regarding a group (e.g., set) of biomarkers 210, which can include a first biomarker (BM1) in column 1 of each matrix, a second biomarker (BM2) in column 2 of each matrix, a third biomarker (BM3) in column 3 of each matrix, and a fourth biomarker (BM4) in column 4 of each matrix, associated with the medical condition that have been determined, based on domain knowledge information relating to the medical condition, to be useful in indicating a risk of onset of the medical condition or progression of the medical condition. With regard to the particular example of type 1 diabetes, the group of biomarkers can be or can comprise islet autoantibodies (IAB) where, for example, the first biomarker can be insulin autoantibodies (IAA), the second biomarker can be islet tyrosine phosphatase 2 antibodies (IA-2A), the third biomarker can be glutamic acid decarboxylase antibodies (GADA), and the fourth biomarker can be zinc transporter 8 autoantibodies (Znt8A). It is to be appreciated and understood that, with regard to another type of medical condition, there can be different biomarkers and/or a different number of biomarkers that can be useful in indicating a risk of onset of such other type of medical condition or progression of such other type of medical condition.

Each row of a set of rows of each matrix (e.g., matrix 202 and matrix 206) can relate to respective times (e.g., times 212 and times 214) of clinical visits (e.g., time period 1, time period 2, time period 3, time period 4, time period 5, and/or time period 6) by subject A 204 and subject B 208 where the testing for the group of biomarkers has been performed. In the matrices 200, a "1" value can indicate the lab test result relating to that biomarker was positive and a "0" value can indicate the lab test result relating to that biomarker was negative. It is to be appreciated and understood that, while a binary result of positive or negative is used in the example matrices 200, in accordance with other embodiments, the disclosed subject matter can utilize a desired level of granularity with regard to the lab test results relating to biomarkers. For example, the ontology generator component 102 can utilize a "0" indicator to indicate a negative test result relating to a biomarker, a "low" indicator or value (e.g., "1") to indicate a positive test result at a relatively lower level of positivity with regard to the biomarker, a "medium" indicator or value (e.g., "2") to indicate a positive test result at a medium level of positivity with regard to the biomarker, and a "high" indicator or value (e.g., "3") to indicate a positive test result at a relatively higher level of positivity with regard to the biomarker. As another example, the ontology generator component 102 can utilize a set of values ranging from 0 to 10, or 0 to 100, to indicate no positivity (e.g., a "0" value) or a relative level of positivity ranging from relatively low (e.g., a "1" value) to a relatively high value (e.g., a "10" value when the range is 0 to 10; or a "100" value when the range is 0 to 100) with regard to the biomarker. The ontology developer component 108 can accordingly structure an ontology 104 relating to a medical condition, including the number of nodes, the types of nodes, and/or the arrangement of the nodes in the ontology 104, to take into account the higher level of granularity with regard to the lab test results relating to biomarkers.

With regard to subject A 204, as can be observed in the matrix 202, at time period 1 (e.g., with regard to clinical visit 1) subject A 204 tested negative for all four biomarkers, at time period 2 (e.g., with regard to clinical visit 2), subject A 204 tested positive for the second biomarker and negative for the other three biomarkers, at time period 3 (e.g., with regard to clinical visit 3), subject A 204 tested positive for the third biomarker and negative for the other biomarkers, at time period 4 (e.g., with regard to clinical visit 4), subject A 204 tested positive for the first biomarker and again for third biomarker, and tested negative for the second and fourth biomarkers, and at time period 5 (e.g., with regard to clinical visit 5) subject A 204 tested negative for all four biomarkers. From the biomarker test results in the matrix 202, the ontology generator component 102 can determine that, at time period 2, subject A 204 had developed a single positive biomarker (e.g., the second biomarker), with no previous positive biomarkers, and, accordingly, can assign a label of Single to clinical visit 2 for subject A 204. Also, from the biomarker test results in the matrix 202, the ontology generator component 102 can determine that, at time period 3, subject A 204 had developed a different single positive biomarker (e.g., the third biomarker), with a different previous positive biomarker (e.g., the second biomarker during clinical visit 2), and, accordingly, since there were different positive biomarkers that were positive during different clinical visits, the ontology generator component 102 can assign a label of Multiple (or Multiple IAB with regard to type 1 diabetes) to clinical visit 3 for subject A 204. Further, from the biomarker test results in the matrix 202, the ontology generator component 102 can determine that, at time period 4, subject A 204 had developed multiple positive biomarkers (e.g., the first and third biomarkers), with one of those positive biomarkers (e.g., the third biomarker) being positive over two consecutive clinical visits (e.g., clinical visits 3 and 4), and, accordingly, since there subject A 204 had positive lab test results for the third biomarker over two consecutive clinical visits, the ontology generator component 102 can assign a label of MultiplePersistentOR to clinical visit 4 for subject A 204.

With regard to subject B 208, as can be observed in the matrix 206, at time period 1 (e.g., with regard to clinical visit 1) subject B 208 tested positive for the second biomarker and negative for the other three biomarkers, at time period 2 (e.g., with regard to clinical visit 2), subject B 208 tested positive for the second biomarker again and negative for the other biomarkers, at time period 3 (e.g., with regard to clinical visit 3), subject B 208 tested negative for all four biomarkers, at time period 4 (e.g., with regard to clinical visit 4), subject B 208 tested positive for the second biomarker and third biomarker, and tested negative for the first and fourth biomarkers, at time period 5 (e.g., with regard to clinical visit 5) subject B 208 again tested positive for the second biomarker and third biomarker, and tested negative for the first and fourth biomarkers, and at time period 6 (e.g., with regard to clinical visit 6), subject B 208 tested negative for all four biomarkers. From the biomarker test results in the matrix 206, the ontology generator component 102 can determine that, at time period 1, subject B 208 had developed a single positive biomarker (e.g., the second biomarker), with no previous positive biomarkers, and, accordingly, can assign a label of Single to clinical visit 1 for subject B 208. Also, from the biomarker test results in the matrix 206, the ontology generator component 102 can determine that, at time period 2, subject B 208 had tested positive again for the same single biomarker (e.g., the second biomarker), with no other positive biomarkers, and, accordingly, since subject B 208 tested positive for the same biomarker during two consecutive clinical visits, the ontology generator component 102 can assign a label of SinglePersistent to clinical visit 2 for subject B 208. Further, from the biomarker test results in the matrix 206, the ontology generator component 102 can determine that, at time period 4, subject B 208 had developed multiple positive biomarkers (e.g., the second and third biomarkers) during clinical visit 4, with neither of those biomarkers being positive during the previous clinical visit (e.g., clinical visit 3), and, accordingly, since subject B 208 had positive lab test results for multiple biomarkers during the same clinical visit, the ontology generator component 102 can assign a label of Multiple@SameVisit to clinical visit 4 for subject B 208. Also, from the biomarker test results in the matrix 206, the ontology generator component 102 can determine that, at time period 5, subject B 208 had developed multiple positive biomarkers (e.g., the second and third biomarkers) during clinical visit 5 as well as previous clinical visit 4, and, accordingly, since subject B 208 was determined to have positive lab test results for the same two biomarkers during two consecutive clinical visits, the ontology generator component 102 can assign a label of MultiplePersistentAND to clinical visit 5 for subject B 208.

In some embodiments, the ontology developer component 108 can rank the respective nodes 110 and associated statuses (e.g., the edges between nodes) relating to the medical condition according to the respective severity of the respective nodes and associated statuses and/or respective progression and severity of the medical condition based on the domain knowledge information (e.g., clinical knowledge information) relating to the medical condition (e.g., as provided by one or more medical experts with regard to the medical condition). For example, when there is a node relating to positivity of a biomarker relating to the medical condition, the ontology developer component 108 can rank the node that is a single positive biomarker (e.g., Single) as a lowest in level of severity with regard to the medical condition (although having no positive biomarker relating to the medical condition can have a lower level of severity with regard to the medical condition than having a single positive biomarker relating to the medical condition). As another example, the ontology developer component 108 can rank the node regarding a single type of biomarker that is persistent (e.g., SinglePersistent) as more severe, and accordingly, a higher rank in the ontology, than the node that is associated with the single positive biomarker (e.g., Single). As still another example, the ontology developer component 108 can rank the node regarding multiple types of positive biomarkers (e.g., Multiple or MultipleIAB) cumulatively over clinical visits as more severe, and accordingly, a higher rank in the ontology, than the node associated with the single type of biomarker that is persistent (e.g., SinglePersistent).

As yet another example, the ontology developer component 108 can rank the node regarding multiple positive biomarkers during the same visit (e.g., Multiple@SameVisit) as more severe, and accordingly, a higher rank in the ontology, than the node that is associated with the multiple types of positive biomarkers (e.g., Multiple or MultipleIAB) cumulatively over clinical visits. As still another example, the ontology developer component 108 can rank the node regarding multiple positive biomarkers and persistent with regard to a single biomarker (e.g., MultiplePersistentOR) relating to the medical condition as more severe, and accordingly, a higher rank in the ontology, than the node associated with the multiple positive biomarkers during the same visit (e.g., Multiple@SameVisit). As yet another example, the ontology developer component 108 can rank the node regarding multiple positive biomarkers and persistent with regard to the same multiple biomarkers (e.g., MultiplePersistentAND) relating to the medical condition as more severe, and accordingly, a higher rank in the ontology, than the node associated with the multiple positive biomarkers and persistent with regard to a single biomarker (e.g., MultiplePersistentOR) relating to the medical condition. It is to be appreciated and understood that this ranking of the nodes 110 and associated statuses is a non-limiting example of ranking of nodes and statuses relating to a medical condition, and, in accordance with various aspects and embodiments, with regard to a particular medical condition, the ontology developer component 108 can determine a different (or same) group of nodes 110 and/or a different (or same) ranking of nodes 110 and associated statuses relating to the particular medical condition based on the results of analyzing clinical feature data relating to clinical features of patients and particular domain knowledge information relating to the particular medical condition.

Figure 3:
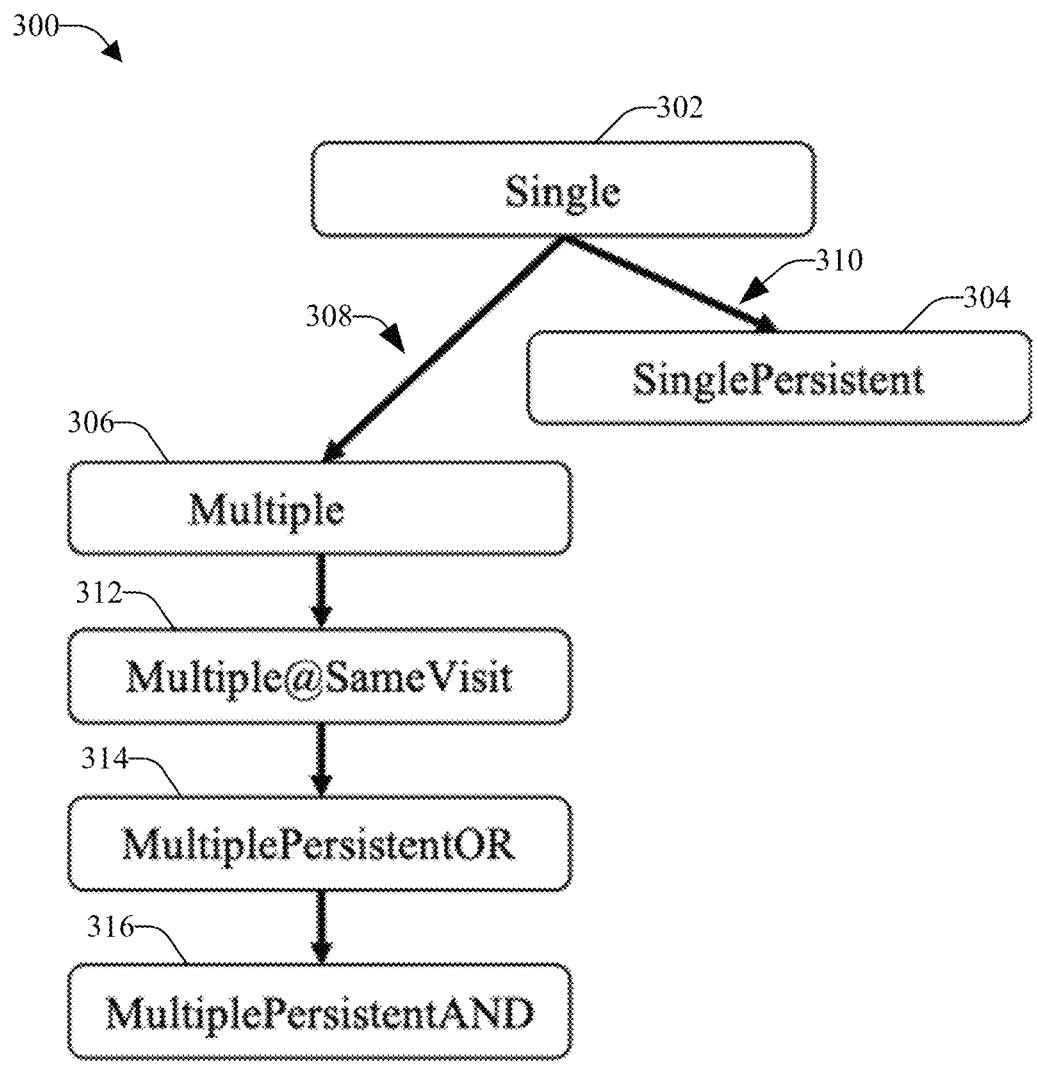
FIG. 3 illustrates a diagram of an example ontology relating to a medical condition, in accordance with various aspects and embodiments of the disclosed subject matter.

Referring to FIG. 3 (along with FIG. 1), FIG. 3 illustrates a diagram of an example ontology 300 relating to a medical condition, in accordance with various aspects and embodiments of the disclosed subject matter. The example ontology 300 can relate to and be applicable to, for example, a medical condition (e.g., disease) such as type 1 diabetes. The ontology developer component 108 can rank, arrange, and/or structure the nodes of the ontology 300 relative to each other, and the associated statuses (e.g., the edges between nodes) relating to the medical condition, according to the respective severity of the respective nodes and associated statuses and/or respective progression and severity of the medical condition based on the domain knowledge information (e.g., clinical knowledge information) relating to the medical condition (e.g., as provided by one or more medical experts with regard to the medical condition).

For instance, in the example ontology 300, the ontology developer component 108 can structure the ontology 300 to comprise a Single node 302, which can be the lowest stringent biomarker risk definition and medical status (other than having no positive biomarkers relating to the medical condition). Accordingly, the ontology developer component 108 can place the Single node 302 at the top of the ontology 300, which can indicate that the Single node 302 is associated with the lowest level of severity or risk, and/or lowest stringent biomarker risk definition, with regard to onset of medical condition (e.g., type 1 diabetes), relative to the other nodes of the ontology 300.

The ontology developer component 108 can structure the ontology 300 to comprise a SinglePersistent node 304, which can relate to a case where a subject has tested positive for the same biomarker during two consecutive tests. The SinglePersistent node 304 can be a relatively lower stringent biomarker risk definition and medical status, but can represent a higher level of stringency, severity, or risk with regard to the medical condition than the single status (e.g., single positive biomarker status with no prior positive biomarker test results) associated with the Single node 302. Accordingly, the ontology developer component 108 can place the SinglePersistent node 304 in a position within the ontology 300 that can be lower (e.g., further down) than (e.g., corresponding to a higher or deeper rank than) the position of the Single node 302 to indicate that the SinglePersistent node 304 is associated with a relatively higher level stringency, severity, or risk with regard to the medical condition than the single status associated with the Single node 302.

The ontology developer component 108 can structure the ontology 300 to comprise a Multiple node 306, which can relate to a case where a subject was determined to have tested positive cumulatively for more than one type of biomarker (e.g., multiple biomarkers) relating to the medical condition over two clinical visits (e.g., the subject tested positive for one type of biomarker during one clinical visit and tested positive for another type of biomarker during a next clinical visit). The Multiple node 306 can represent a relatively higher level of stringency, severity, or risk with regard to the medical condition than the single and persistent status associated with the SinglePersistent node 304. Accordingly, the ontology developer component 108 can place the Multiple node 306 in a position within the ontology 300 that can be lower than (e.g., corresponding to a higher or deeper rank than) the position of the SinglePersistent node 304 to indicate that the Multiple node 306 is associated with a relatively higher level stringency, severity, or risk with regard to the medical condition than the single and persistent status associated with the SinglePersistent node 304. It is noted though that, in some embodiments, the ontology developer component 108 can place the Multiple node 306 along a different branch 308 (e.g., and associated edge) than the branch 310 (e.g., and associated edge) associated with the SinglePersistent node 304, as depicted in the ontology 300, wherein the Multiple node 306 can be in a lower spatial position than the SinglePersistent node 304.

The ontology developer component 108 also can structure the ontology 300 to comprise a Multiple@SameVisit node 312, which can relate to a case where a subject was determined to have tested positive for two different biomarkers relating to the medical condition during the same clinical visit. The Multiple@SameVisit node 312 can represent a relatively higher level of stringency, severity, or risk with regard to the medical condition than the multiple status associated with the Multiple node 306. Accordingly, the ontology developer component 108 can place the Multiple@SameVisit node 312 in a position within the ontology 300 that can be lower than the position of the Multiple node 306 to indicate that the Multiple@SameVisit node 312 is associated with a relatively higher level stringency, severity, or risk with regard to the medical condition than the single and persistent status associated with the Multiple node 306.

The ontology developer component 108 further can structure the ontology 300 to comprise a MultiplePersistentOR node 314, which can relate to a case where a subject was determined to have tested positive for two different biomarkers relating to the medical condition during a same clinical visit where one of those biomarkers is persistent because the subject tested positive for that biomarker during two (or more) consecutive visits. The MultiplePersistentOR node 314 can represent a relatively higher level of stringency, severity, or risk with regard to the medical condition than the status relating to multiple positive biomarkers during the same clinical visit status that can be associated with the Multiple@SameVisit node 312. Accordingly, the ontology developer component 108 can place the MultiplePersistentOR node 314 in a position within the ontology 300 that can be lower than the position of the Multiple@SameVisit node 312 to indicate that the MultiplePersistentOR node 314 is associated with a relatively higher level stringency, severity, or risk with regard to the medical condition than the single and persistent status associated with the Multiple@SameVisit node 312.

The ontology developer component 108 also can structure the ontology 300 to comprise a MultiplePersistentAND node 316, which can relate to a case where a subject was determined to have tested positive for two (or more) different biomarkers during two (or more) consecutive visits. The MultiplePersistentAND node 316 can represent a relatively higher level (e.g., the highest level in the example ontology 300) of stringency, severity, or risk with regard to the medical condition than the medical condition status associated with the MultiplePersistentOR node 314. Accordingly, the ontology developer component 108 can place the MultiplePersistentAND node 316 in a position within the ontology 300 that can be lower than the position of the MultiplePersistentOR node 314 to indicate that the MultiplePersistentAND node 316 is associated with a relatively higher level stringency, severity, or risk with regard to the medical condition than the single and persistent status associated with the MultiplePersistentOR node 314.

It is to be appreciated and understood that the ontology 300 is a non-limiting example ontology. With regard to different types of medical conditions, the disclosed subject matter (e.g., the ontology generator component 102) can develop unique and/or different ontologies with regard to those different types of medical conditions, wherein respective ontologies associated with respective ontologies can have respective (e.g., unique and/or different) numbers of nodes, types of nodes, and/or arrangements of nodes, in accordance with the defined ontology development and management criteria and associated defined ontology development and management algorithms, such as described herein with regard to the techniques and methods disclosed herein. For example, based on a first analysis of first clinical profiles, comprising first clinical features (e.g., first biomarkers and/or other first clinical features), and first domain knowledge relating to a first medical condition, associated with a first group of persons, the ontology developer component 108 can determine and/or develop a first ontology relating to the first medical condition, wherein the first ontology can comprise a first group of nodes and a first ranking of nodes of the first group of nodes. Based on a second analysis of second clinical profiles, comprising second clinical features (e.g., second biomarkers and/or other second clinical features), and second domain knowledge relating to a second medical condition, associated with a second group of persons, the ontology developer component 108 can determine and/or develop a second ontology relating to the second medical condition, wherein the second ontology can comprise a second group of nodes and a second ranking of nodes of the second group of nodes, wherein the second ontology can be different from (or same as) the first ontology.

In some embodiments, the ontology developer component 108 can determine, derive, and/or develop a group of global features (e.g., global temporal features), comprising one or more global features 112, relating to the medical condition based at least in part on the ontology (e.g., ontology 104, or ontology 300). For example, based on the ontology (e.g., ontology 104, or ontology 300) relating to the medical condition, the ontology developer component 108 can determine and/or develop desired global features 112, such as a highest risk so far (HighestRiskSoFar) and a pathway length to the highest risk so far (PathwayLengthToHighestRiskSoFar; also referred to herein as the pathway global feature), relating to the medical condition (e.g., type 1 diabetes or other type of medical condition). The disclosed subject matter can define the highest-risk-so-far global feature as the highest level of risk relating to the medical condition that a subject (e.g., a patient) has reached up to an index time (also referred to as IndexTime), which can be a time that a prediction or forecast is going to be made regarding the subject's risk of onset of the medical condition, if the subject does not yet have the medical condition, or risk of progression of the medical condition, if the subject already has the medical condition. The highest-risk-so-far global feature can represent or be associated with the deepest node in the ontology (e.g., ontology 104, or ontology 300) that the subject's health condition has reached at the index time.

For example, with regard to subject A 204, if the index time is time period 4, the ontology generator component 102 can determine that the highest-risk-so-far global feature for subject A 204 at time period 4 can be MultiplePersistentOR, since, based on the ontology, MultiplePersistentOR can be the highest risk that subject A 204 has reached up to that index time. As another example, with regard to subject B 208, if the index time is time period 5, the ontology generator component 102 can determine that the highest-risk-so-far global feature for subject B 208 at time period 5 can be MultiplePersistentAND, since, based on the ontology, MultiplePersistentAND can be the highest risk that subject B 208 has reached up to that index time (e.g., time period 5).

The disclosed subject matter can define the pathway global feature as the length of the trajectory to the subject attaining (e.g., reaching) the highest risk so far (e.g., current risk) relating to the medical condition. The pathway length can relate to the temporal length (e.g., the amount of time) it took the subject to attain the highest risk so far relating to the medical condition and/or the nodal length (e.g., the length of the path from the first node to the deepest node) that the subject's health condition has traveled in reaching the highest risk so far relating to the medical condition. Different persons can have different paths or trajectories to reach a specific risk relating to a medical condition.

For example, with regard to subject A 204, if the index time is time period 4, the ontology generator component 102 can determine or identify that the path associated with subject A 204 developed from Single status to Multiple status to MultiplePersistentOR status over a period of three consecutive clinical visits (e.g., from clinical visit 2 through clinical visit 4). Accordingly, the ontology generator component 102 can determine the path global feature associated with subject A 204 as being a path or trajectory spanning from Single status to Multiple status to MultiplePersistentOR status over that time period spanning those three consecutive clinical visits. As another example, with regard to subject B 208, if the index time is time period 5, the ontology generator component 102 can determine or identify that the path associated with subject B 208 developed from Single status to SinglePersistent status to Multiple@SameVisit status to MultiplePersistentAND status over a period of five consecutive clinical visits (e.g., from clinical visit 1 through clinical visit 5). Accordingly, the ontology generator component 102 can determine the path global feature associated with subject B 208 as being a path or trajectory spanning from Single status to SinglePersistent status to Multiple@SameVisit status to MultiplePersistentAND status over that time period spanning those five consecutive clinical visits.

It is to be appreciated and understood that the highest-risk-so-far global feature and the pathway global feature are non-limiting example global features that can be utilized by the disclosed subject matter (e.g., the ontology generator component 102 and/or other components of the disclosed subject matter). In accordance with various embodiments, the disclosed subject matter can develop and utilize other types of global features 112 based on an ontology (e.g., ontology 104, or ontology 300), wherein the types of global features can be based on the type of ontology, the type of medical condition associated with (e.g., represented by) the ontology, the type of forecast or prediction being made using the ontology and global features, and/or other factors.

In some embodiments, in addition to the global features 112, the ontology developer component 108 (or other component of the ontology generator component 102) can determine, develop, and/or extract one or more other desired (e.g., relevant or suitable) features, such as, for example, dynamic biomarkers (biomarker_dyn, such as, e.g., BM1_dyn, BM2_dyn, BM3_dyn, or BM4_dyn), biomarker counts (BiomarkerCounts, CumulativeCount (e.g., CumulativeIABCount with regard to type 1 diabetes), or other similarly named term relating to counts, such as cumulative counts, associated with positive tests for biomarkers), and/or another feature, relating to the medical condition based on the ontology (e.g., ontology 104, or ontology 300) and/or information obtained from another data source(s) and relating to the medical condition. The ontology developer component 108 (or other component of the ontology generator component 102) can determine a variety of desired features, including dynamic and/or global features.

For example, with regard to type 1 diabetes, the disclosed subject matter (e.g., the ontology generator component 102 or a user(s)) can determine a set of basic features and a set of dynamic features, such as those features presented in Table 1.

TABLE 1

Basic Feature Set

| Feature | Description |
| --- | --- |
| Age | Age at index time |
| ABcount_n | Number of positive ABs at index time |
| Biological characteristic | Biological characteristic of the subject: first type (0), second type (1) |
| Site A study | If the subject was enrolled in Site A study (1) or not (0) |
| Site B study | If the subject was enrolled in Site B study (1) or not (0) |
| Site C study | If the subject was enrolled in Site C study (1) or not (0) |
| HLA GROUP A | If the subject was classified as high risk group A (1) or not (0) |
| HLA GROUP B | If the subject was classified as risk group B (1) or not (0) |
| HLA GROUP C | If the subject was classified as risk group C (1) or not (0) |
| HLA GROUP D | If the subject was classified as low risk group D (1) or not (0) |
| BM1 | If the subject was tested positive for BM1 (1) or not (0) at index time |
| BM2 | If the subject was tested positive for BM2 (1) or not (0) at index time |
| BM3 | If the subject was tested positive for BM3 (1) or not (0) at index time |
| BM4 | If the subject was tested positive for BM4 (1) or not (0) at index time |

Dynamic Feature Set

| Feature | Description |
| --- | --- |
| BM1_dyn | If BM1 was tested differently for the subject between firstBiomarker and indexTime: −1 positive at firstBiomarker but ever became negative between firstBiomarker and indexTime, 1 vice versa, 0 no change between firstBiomarker and indexTime |
| BM2_dyn | If BM2 was tested differently for the subject between firstBiomarker and indexTime: −1 positive at firstBiomarker but ever became negative between firstBiomarker and indexTime, 1 vice versa, 0 no change between firstBiomarker and indexTime |
| BM3_dyn | If BM3 was tested differently for the subject between firstBiomarker and indexTime: −1 positive at firstBiomarker but ever became negative between firstBiomarker and indexTime, 1 vice versa, 0 no change between firstBiomarker and indexTime |
| BM4_dyn | If BM4 was tested differently for the subject between firstBiomarker and indexTime: −1 positive at firstBiomarker but ever became negative between firstBiomarker and indexTime, 1 vice versa, 0 no change between firstBiomarker and indexTime |
| CumulativeIABCount | How many kinds of IAB were ever tested positive for a subject between firstBiomarker and indexTime |
| HighestRiskSoFar | The highest risk (e.g. the deepest node in the IAB ontology) that a subject has reached up to indexTime |
| PathwayLengthToHighestRiskSofar | The length of the trajectory to the HighestRiskSoFar |

In Table 1, AB can refer to antibodies, firstBiomarker can refer to a time of a first positive biomarker, indexTime can refer to an index time, and other terms can be as described within Table 1 or as otherwise described herein. It is to be appreciated and understood that, in accordance with the disclosed subject matter, respective (e.g., different) types of medical conditions can have or be associated with respective types or respective numbers of dynamic or global features, or respective types or numbers of basic features.

In certain embodiments, at a desired index time (e.g., forecasting or prediction time), and with regard to a desired person (e.g., subject or patient), the ontology generator component 102, employing the feature extractor component 106, can extract one or more global features 112 (e.g., highest-risk-so-far global feature, pathway global feature, or other global feature) from the ontology (e.g., ontology 104, or ontology 300) and/or one or more other features from the ontology and/or another data source(s), based on the results of an analysis of the ontology and/or clinical features (e.g., lab results, biomarkers, commodities, medications, or other clinical features) relating to the person. The one or more global features 112 and/or the other features can be applied to a desired prediction model to facilitate predicting a time when the person may develop the medical condition, if the person has not already developed the medical condition, or predicting progression of the medical condition in the person, if the person already has the medical condition, as more fully described herein. The predictions obtained from the prediction model using the one or more global features 112 obtained from the ontology described herein and/or the other features can be enhanced (e.g., improved, more accurate, and/or optimized), as compared to predictions made using existing techniques.

Figure 4:
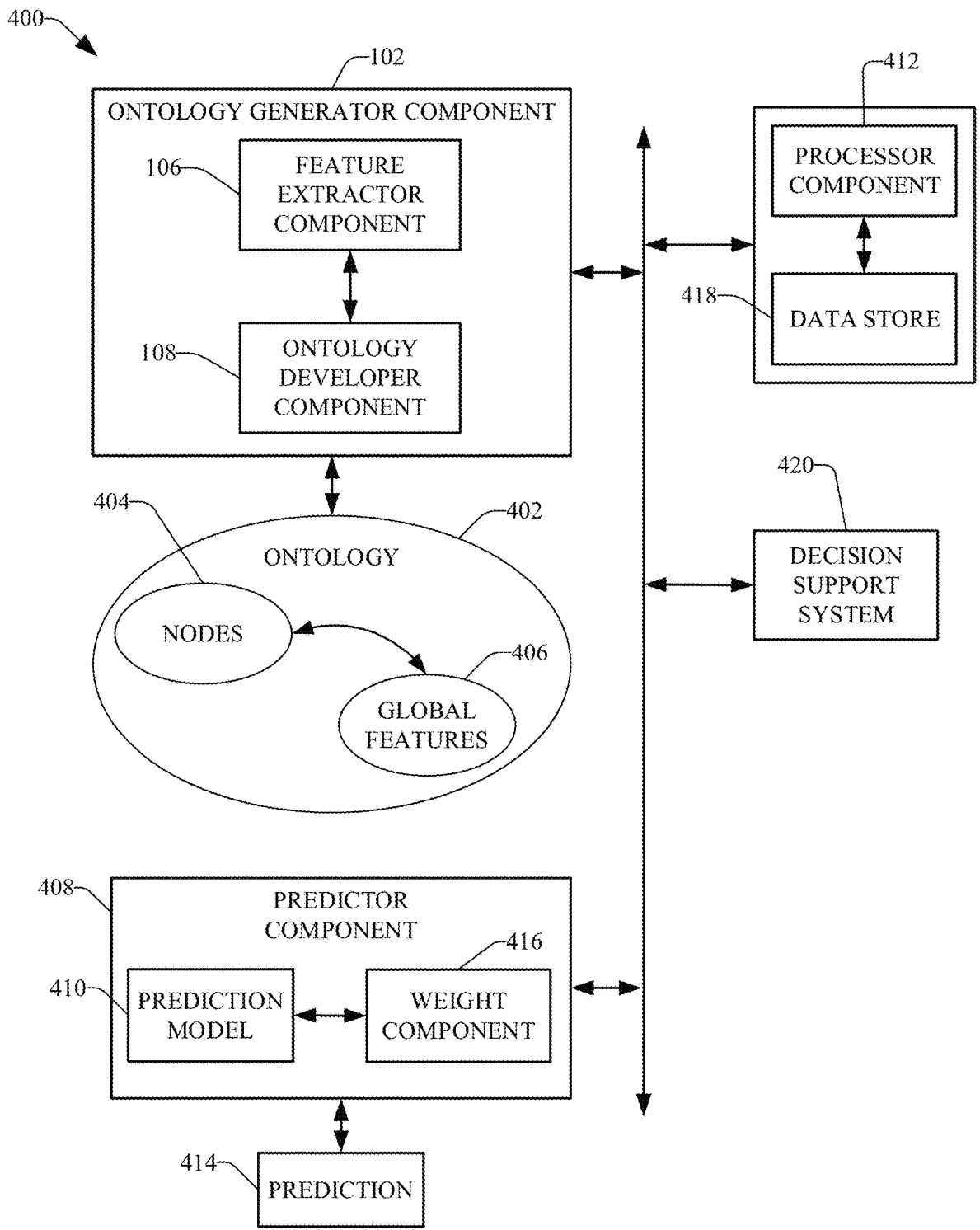
FIG. 4 depicts a diagram of an example, non-limiting system that can develop an ontology and can utilize information from the ontology to enhance a prediction relating to a medical condition associated with a person, in accordance with various aspects and embodiments of the disclosed subject matter.

Referring to FIG. 4, FIG. 4 depicts a diagram of an example, non-limiting system 400 that can develop an ontology and can utilize information from the ontology to enhance a prediction relating to a medical condition associated with a person, in accordance with various aspects and embodiments of the disclosed subject matter. The system 400 can comprise the ontology generator component 102 that can determine, develop, and/or generate ontologies relating to medical conditions, such an ontology 402 relating to a medical condition, based on medical data relating to a group of persons and respective domain knowledge information relating to the respective medical conditions, such as more fully described herein. The ontology generator component 102 can comprise the feature extractor component 106 and ontology developer component 108, such as described herein. The ontology 402 can comprise a group of nodes 404, which can be determined, developed, ranked, and/or arranged by the ontology generator component 102 and can be unique to the medical condition, as more fully described herein. At desired times (e.g., index or prediction time), the ontology generator component 102 can extract a group of global features 406, comprising one or more global features, relating to the medical condition and a subject (e.g., person or patient) based on the ontology 402 and medical information (e.g., clinical profile data relating to clinical features) relating to the subject, such as more fully described herein.

The system 400 also can comprise a predictor component 408 that can be associated with the ontology generator component 102. In some embodiments, the predictor component 408 can be communicatively connected to the ontology generator component 102 to enable the predictor component 408 to receive information (e.g., information relating to global features 406) relating to an ontology (e.g., ontology 402) regarding a medical condition and/or other desired information (e.g., information relating to clinical or other features) relating thereto. In certain embodiments, the predictor component 408 can receive such information relating to the ontology regarding the medical condition from another data source that can receive such information, directly or indirectly, from the ontology generator component 102.

The predictor component 408 can comprise one or more prediction models, such as prediction model 410, and can employ one or more prediction algorithms to perform predictions relating to medical conditions. At a desired index time (e.g., a forecasting or prediction time), with regard to a subject (e.g., person or patient), the ontology generator component 102 can extract the one or more global features 406 and/or the other features from the ontology 402 (and/or another data source) in relation to the subject based on the results of an analysis of the information contained in the ontology 402 and/or information relating to clinical features (e.g., lab results, biomarkers, commodities, medications, or other clinical features) regarding the subject. The ontology generator component 102 (or another component, such as processor component 412) can apply or input the information relating to one or more global features 406 and/or the information relating to the other features to the prediction model 410 and/or can train the prediction model 410 based on the information relating to the one or more global features 406 and/or the information relating to the other features.

Based on the application of the information relating to the one or more global features 406 and/or the information relating to the other features to the prediction model 410, and/or based on the training of the prediction model 410, the prediction model 410 can predict a level of risk that the subject will develop the medical condition and/or a time (e.g., within a period of months or years from the index time) of an onset of the medical condition in the subject, if the subject does not yet have the medical condition, or can predict a progression of the medical condition in the subject over time, if the subject already has the medical condition. The prediction model 410 can generate predictions, such as prediction 414, as an output.

In some embodiments, the predictor component 408 can comprise a weight component 416 that can apply respective weights to respective indicators (e.g., respective global features, other respective dynamic features, or other respective features) associated with the medical condition to facilitate further improving predictions (e.g., prediction 414) relating to medical conditions made by the prediction model 410, in accordance with defined prediction management criteria. For instance, the predictor component 408 (or another component or a user) can determine that a first global feature relating to a medical condition can be a better indicator or predictor of a time of onset of the medical condition in a subject than a second global feature relating to the medical condition. Accordingly, the weight component 416 (or another component or a user) can apply a first weight (e.g., first weight value) to the first global feature and a second weight to the second global feature, wherein the first weight can be relatively higher than the second weight. As a result, when making a prediction, the prediction model 410 can determine a prediction relating to the medical condition with regard to a subject that can be based on (e.g., influenced, modified, or adjusted by) the first weight applied to the first global feature and the second weight applied to the second global feature.

The predictor component 408 can provide (e.g., communicate or display (e.g., via a desired interface, such as a display screen)) the prediction 414 relating to the medical condition and associated subject. The predictions (e.g., prediction 414) obtained from the prediction model 410 using the one or more global features 406 obtained from the ontology 402 and/or the other features can be enhanced (e.g., improved, more accurate, and/or optimized), as compared to predictions made using existing techniques.

The system 400 can comprise the processor component 412 and a data store 418 that can be associated with (e.g., communicatively connected to) the ontology generator component 102 and/or the predictor component 408. The processor component 412 can work in conjunction with the other components (e.g., ontology generator component 102, predictor component 408, data store 418, and/or other component) to facilitate performing the various functions of the system 400. The processor component 412 can employ one or more processors, microprocessors, or controllers that can process data, such as information relating to clinical features or profiles associated with subjects, domain knowledge information relating to medical conditions, ontologies, nodes, ranking of nodes, global, dynamic, or other features, prediction models, predictions relating to medical conditions associated with subjects, applications, defined ontology development and management criteria, defined ontology development and management algorithms, defined prediction management criteria, defined prediction algorithms, traffic flows, policies, protocols, interfaces, tools, and/or other information, to facilitate operation of the system 400, as more fully disclosed herein, and control data flow between the system 400 and other components (e.g., computer, laptop computer, or other computing or communication device) associated with (e.g., connected to) the system 400.

The data store 418 can store data structures (e.g., user data, metadata), code structure(s) (e.g., modules, objects, hashes, classes, procedures) or instructions, information relating to clinical features or profiles associated with subjects, domain knowledge information relating to medical conditions, ontologies, nodes, ranking of nodes, global, dynamic, or other features, prediction models, predictions relating to medical conditions associated with subjects, applications, defined ontology development and management criteria, defined ontology development and management algorithms, defined prediction management criteria, defined prediction algorithms, traffic flows, policies, protocols, interfaces, tools, and/or other information, to facilitate controlling operations associated with the system 400. In an aspect, the processor component 412 can be functionally coupled (e.g., through a memory bus) to the data store 418 in order to store and retrieve information desired to operate and/or confer functionality, at least in part, to the ontology generator component 102, predictor component 408, data store 418, and/or other component, and/or substantially any other operational aspects of the system 400.

In certain embodiments, the ontology generator component 102, the predictor component 408, the processor component 412, and/or the data store 418 can be associated with (e.g., communicatively connected to) or integrated with a decision support system 420 (e.g., a decision support system comprising or associated with an EMR system) to facilitate improving accuracy of predictions relating to medical conditions. For instance, associating or integrating the ontology generator component 102, the predictor component 408, the processor component 412, and/or the data store 418 with the decision support system 420 to enable desirable triggering of decision support with regard to patients, for example, when certain decision support criteria is satisfied (e.g., met). This can enable physicians to have access more readily to more accurate predictions relating to medical conditions with regard to patients (e.g., as obtained from prediction models when ontologies, such as described herein, are utilized with the prediction models), and accordingly, with such more accurate predictions the physicians can have the ability to assess a patient's risk with regard to a medical condition more accurately, as compared to existing risk assessments or scores relating to medical conditions.

Figure 5:
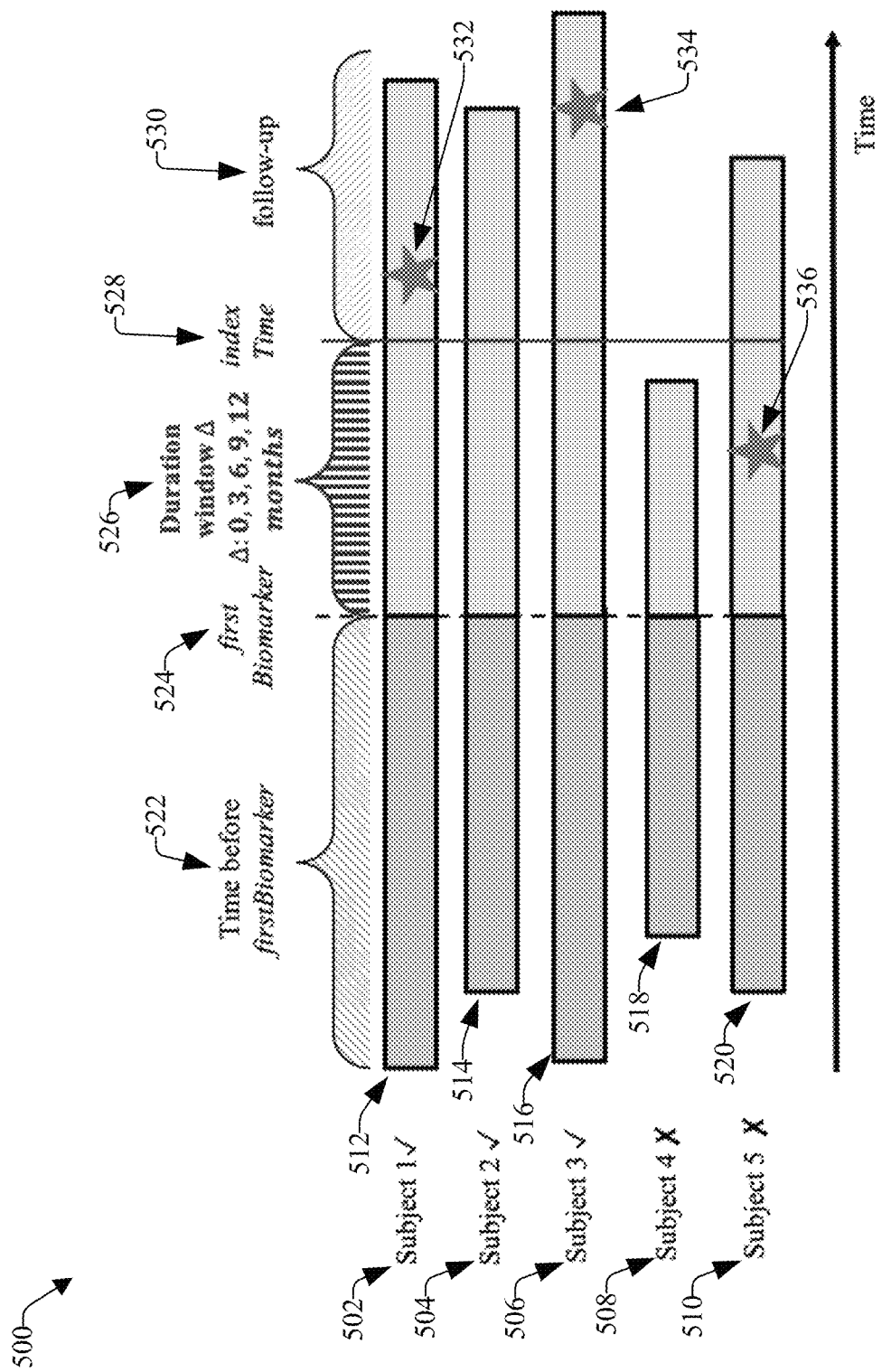
FIG. 5 presents a diagram of an example graph relating to subjects being considered for selection in training a prediction model with regard to a medical condition, in accordance with various aspects and embodiments of the disclosed subject matter.

Turning to FIG. 5 (along with FIGS. 1 and 4), FIG. 5 presents a diagram of an example graph 500 relating to subjects being considered for selection in training a prediction model with regard to a medical condition, in accordance with various aspects and embodiments of the disclosed subject matter. The example graph 500 presents medical data (e.g., clinical profile data) relating to five subjects being considered for selection in training the prediction model (e.g., prediction model 410) with regard to onset of a medical condition (e.g., type 1 diabetes). The five subjects can include, for example, subject 1 502, subject 2 504, subject 3 506, subject 4 508 and subject 5 510. From the respective medical data associated with the respective subjects (e.g., 502, 504, 506, 508, and 510), there can be respective timelines, such as timelines 512, 514, 516, 518, and 520, that can indicate the respective times of respective clinical features associated with the respective subjects with regard to the medical condition. For instance, the respective timelines 512, 514, 516, 518, and 520 can indicate the time before the first positive biomarker 522 for each of the subjects 502, 504, 506, 508, and 510, the time of the first positive biomarker 524 for the subjects 502, 504, 506, 508, and 510, a duration time window 526 between the time of the first positive biomarker 524 and an index time 528 (index time for applying the prediction model), and a follow-up time period 530. The duration time window 526 can be different (e.g., 0, 3, 6, 9, or 12 months) for different subjects (e.g., 502, 504, 506, 508, and 510).

As can be observed from timeline 512 and timeline 516 of the graph 500, with regard to subject 1 502 and subject 3 506, the medical data associated with subject 1 502 extends for a desirable period of time before, during, and after the index time 528, and the medical data associated with subject 3 506 also extends for a desirable period of time before, during, and after the index time 528. The medical data associated with subject 1 502 also indicates that at time 532, during the follow-up time period 530, subject 1 502 was diagnosed with the medical condition, and the medical data associated with subject 3 506 indicates that at time 534, during the follow-up time period 530, subject 3 506 also was diagnosed with the medical condition. However, since subject 1 502 and subject 3 506 were not diagnosed with the medical condition until after the index time 528, and since there is sufficient and suitable medical data for subject 1 502 and subject 3 506, the disclosed subject matter (e.g., the predictor component 408, another component, or a user) can determine that subject 1 502 and subject 3 506 are suitable candidates that can satisfy (e.g., meet or exceed) the defined prediction management criteria (e.g., candidate selection criteria) and therefore can be selected for use in training the prediction model.

As also can be observed from timeline 514 of the graph 500, with regard to subject 2 504, the medical data associated with subject 2 504 extends for a desirable period of time before, during, and after the index time 528. It is also noted that subject 2 504 has not yet been diagnosed with the medical condition. Since there is sufficient and suitable medical data for subject 2 504, the disclosed subject matter (e.g., the predictor component 408, another component, or a user) can determine that subject 2 504 is a suitable candidate that can satisfy the defined prediction management criteria and therefore can be selected for use in training the prediction model.

As further can be observed from timeline 518 of the graph 500, with regard to subject 4 508, the medical data associated with subject 4 508 does not extend to and is not available at the index time 528. Accordingly, the disclosed subject matter can determine that subject 4 508 is not a suitable candidate (e.g., does not satisfy the defined prediction management criteria) for selection in training the prediction model.

As also can be observed from timelines 520 of the graph 500, with regard to subject 5 510, the medical data associated with the subject 5 510 indicates that subject 5 510 was diagnosed with the medical condition at a time 536 that occurs during the duration time window 526 and prior to the index time 528. Accordingly, the disclosed subject matter can determine that the subject 5 510 also is not a suitable candidate for selection in training the prediction model, even though there is available medical data regarding subject 5 510 at index time 528.

With further regard to FIGS. 1-4, and the use of ontologies of the disclosed subject matter with a prediction models to make predictions relating to medical conditions (e.g., type 1 diabetes), the disclosed subject matter presents other aspects relating to the disclosed subject matter and performance (e.g., enhanced performance) of the disclosed ontologies and prediction models. Some of these aspects will be described with regard to an example medical condition, in particular type 1 diabetes (also referred to herein as T1D), and an example ontology developed for T1D using the ontology development techniques, such as more fully described herein.

With regard to prediction models, the objective of time to event analyses can be to predict the time when the subject will develop T1D. However, one of the challenges with these type of analyses can be censored data, e.g., where some subjects are lost to follow up. A prediction model, which can be or can comprise a survival model (e.g., disease survival model), such as a RankSvx model, can address this challenge in a way by optimizing two objective functions simultaneously. The first objective term, which can be similar to the Cox objective function, can be to order event times which is suited to censored data. So, given two subjects, the goal can be to determine which subject is more likely to develop diabetes first. The second objective function can be to predict the actual time of the diagnosis of T1D and this function models the observed data (subjects who actually developed T1D because their time of diagnosis is known). This term is similar to those used in standard generalized regression models.

Let it be assumed that $t_i$ is the time of onset of T1D for patient i or the time of censoring and $x_i$ represents the feature vector used by the prediction model $f$ to predict the onset of T1D. The RankSvx model can optimize the following objective function of Equation (Eq.) (1):

$$\alpha \mathcal{L}_{obs}(t_i, f(x_i|\Theta)) + (1-\alpha) \mathcal{L}_{cen}(t_i, f(x_i|\Theta)) + g(\Theta) \quad \text{Eq. (1)}$$

where $\Theta$ is the parameter of the model $f$, $\alpha$ is a hyperparameter to weight the contribution of each term, and $g$ is a regularization term to prevent overfitting. The function $f$ can predict the actual event time which is implemented as a linear regression function, e.g., $f(x_i|\Theta) = \Theta^T x_i$, and $\mathcal{L}_{obs}$ can be implemented as the mean squared loss function to penalize the prediction error:

$$\mathcal{L}_{obs} = \sum_i \frac{1}{2}(t_i - \Theta^T x_i)^2. \quad \text{Eq. (2)}$$

The second term in Eq. (1) aims to correctly rank the relative risks of two subjects, which can be equal to maximizing the probability of all pairs of subjects whose predicted event times are correctly ordered among all subjects that can actually be ordered. Let it be assumed that $\varepsilon_{i,j}$ represents all pairs of subjects i, j where subject i observed the event and subject j may or may not have observed the event and $t_i \le t_j$. In order to preserve the order of events, the disclosed subject matter can maximize $$\log \prod_{\varepsilon_{ij}} Pr(t_j > t_i|\Theta) = \log \prod_{\varepsilon_{ij}} Pr[f(x_j|\Theta) - f(x_i|\Theta)]. \quad \text{Eq. (3)}$$

The disclosed subject matter can minimize the following log-sigmoid lower bound $$\mathcal{L}_{cen} = -\sum_{i,j \in \varepsilon_{ij}} \log \sigma(f(x_j|\Theta) - f(x_i|\Theta)), \quad \text{Eq. (4)}$$

where $\sigma$ is the sigmoid function. Finally, the regularization term $g(\Theta)$ is the $\ell_2$ norm to penalize the model complexity, which is defined as $g(\Theta) = \|\Theta\|^2$.

As disclosed, the RankSvx model can optimize two different objective functions simultaneously, where one objective function can be related to ordering the events and the other objective function can be related to predicting the actual diagnosis time. The disclosed subject matter used two metrics to evaluate the performance of the RankSvx model for these two objectives. The first evaluation metric is the concordance index (CI) which can measure the proportion of concordant pairs and is one of the most used evaluation metrics for survival models. CI can be defined, for example, as follows in Eq. (5):

$$CI = \frac{1}{N_{test}} \sum_{\varepsilon_{ij}} 1_{f(x_i) < f(x_j)}, \quad \text{Eq. (5)}$$

where $N_{test}$ is the number of comparable pairs in the test dataset and 1 is the indicator function. Higher CI values can indicate better performance.

Figure 6:
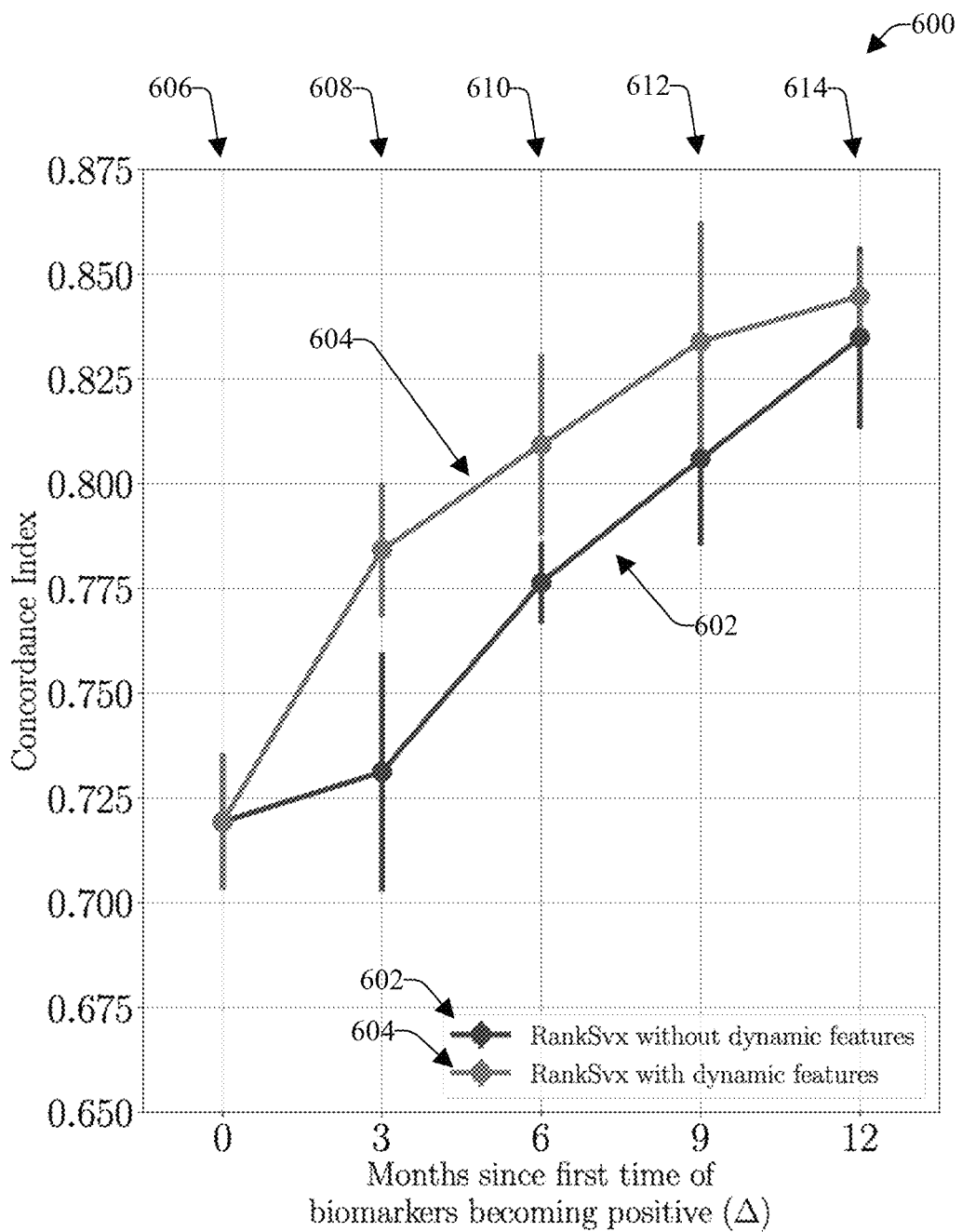
FIG. 6 presents a diagram of a graph of experimental results for a concordance index metric comparing use of basic features with a prediction model and use of dynamic features of the disclosed subject matter with the prediction model and the effect on accuracy of the prediction model, in accordance with various aspects and embodiments of the disclosed subject matter.

Experiments were performed to evaluate whether the clinical information extracted from the ontology of the disclosed subject matter (e.g., using the techniques of the disclosed subject matter, such as described herein) can increase the accuracy of the predictive model. Referring to FIG. 6, FIG. 6 presents a diagram of a graph 600 of experimental results for the CI metric comparing the use of basic features with the prediction model (e.g., the RankSvx model) and the use of the dynamic features of the disclosed subject matter with the prediction model and the effect on accuracy of the prediction model, in accordance with various aspects and embodiments of the disclosed subject matter. The RankSvx model was applied twice: first using only the basic features with the RankSvx model, with the results 602 shown in the graph 600, and second using both the basic features and the dynamic features with the RankSvx model, with the results 604 shown in the graph 600. Different length duration windows (e.g., 0, 3, 6, 9, and 12 months) after the firstBiomarker were explored. Performance at duration window 0 months (as indicated at reference numeral 606) is the same for both the RankSvx model without dynamic features and RankSvx model with dynamic features because there is no dynamic information regarding biomarkers at the first-Biomarker.

With a duration window of 3 months (as indicated at reference numeral 608), it can be observed in the results 602 in the graph 600 that the RankSvx model with only the base features has slightly improved CI performance (from 0.719 to 0.731) compared to 0 months since an additional 3 months of data on the basic features is now available and the indexTime has increased. For the RankSvx model with dynamic features, it can be observed in the results 604 in the graph 600 that the CI performance has significantly increased from 0.719 to 0.784. The difference between RankSvx model with and without dynamic features using a 3-month duration window is 0.053. As further can be observed in the results 602 and 604 of the graph 600, as the duration window increases (as shown at reference numerals 610, 612, and 614, respectively associated with duration windows of 6 months, 9 months, and 12 months), the improvement of the RankSvx model using the dynamic features continues, as the CI metric values associated with the RankSvx model using the dynamic features continue to be higher than the corresponding CI metric values associated with the RankSvx model that did not use the dynamic features. The experimental results (e.g., results 602 and 604) of the graph 600 indicate that the disclosed subject matter, including the ontologies described herein, the techniques for developing ontologies described herein, and extraction of features (e.g., global, dynamic, and/or other features) from ontologies as described herein, can enhance (e.g., improve, increase, or optimize) accuracy of prediction models with regard to predictions of a time of onset of a medical condition in subjects, as compared to existing techniques for making such predictions.

The systems and/or devices have been (or will be) described herein with respect to interaction between several components. It should be appreciated that such systems and components can include those components or sub-components specified therein, some of the specified components or sub-components, and/or additional components. Sub-components could also be implemented as components communicatively coupled to other components rather than included within parent components. Further yet, one or more components and/or sub-components may be combined into a single component providing aggregate functionality. The components may also interact with one or more other components not specifically described herein for the sake of brevity, but known by those of skill in the art.

Figure 7:
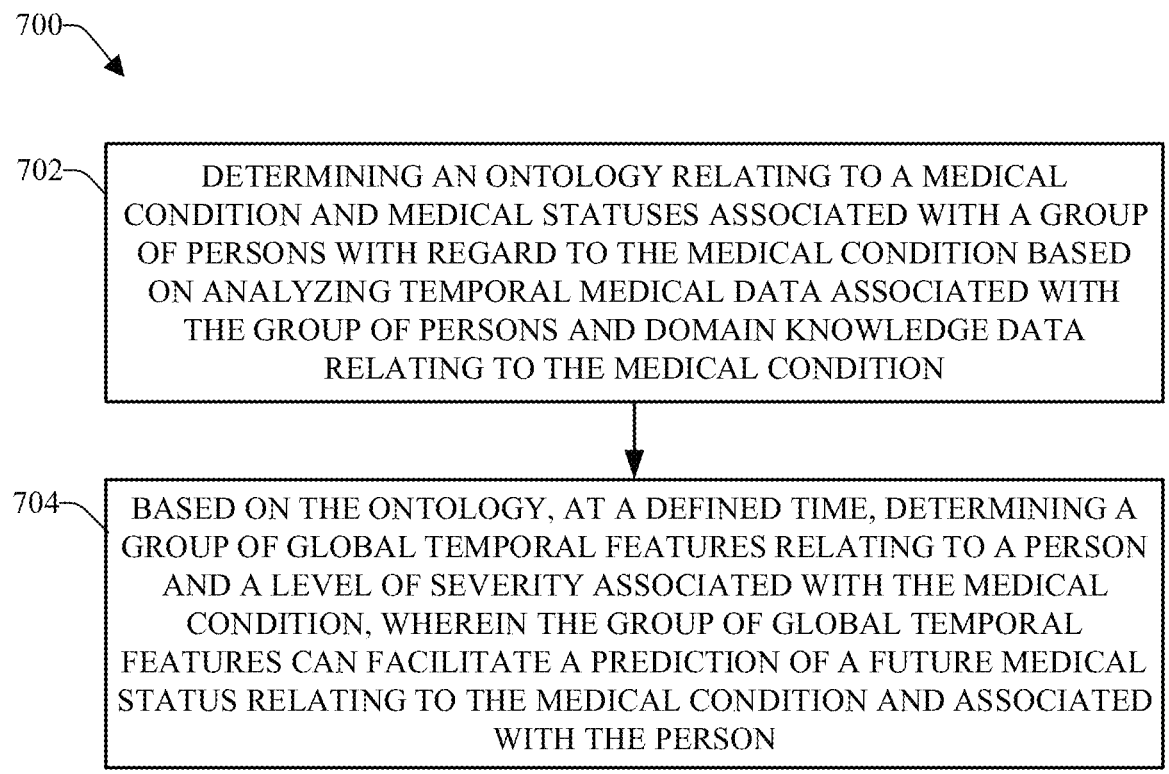
FIG. 7 illustrates a flow diagram of an example, non-limiting method that can determine an ontology based on clinical features, comprising biomarkers, associated with persons to facilitate enhancing clinical predictions relating to a medical condition, in accordance with various aspects and embodiments of the disclosed subject matter.

FIG. 7 illustrates a flow diagram of an example, non-limiting method 700 that can determine an ontology based on clinical features, comprising biomarkers, associated with persons (e.g., patients) to facilitate enhancing clinical predictions relating to a medical condition, in accordance with various aspects and embodiments of the disclosed subject matter. The method 700 can be performed by, for example, a system comprising or operatively coupled to an ontology generator component, a predictor component, and/or a processor component. Repetitive description of like elements employed in other embodiments described herein is or may be omitted for sake of brevity.

At 702, an ontology relating to a medical condition and medical statuses associated with a group of persons with regard to the medical condition can be determined based on analyzing temporal medical data associated with the group of persons and domain knowledge data relating to the medical condition. The ontology generator component, employing the ontology developer component, can determine, develop, and/or generate the ontology relating to the medical condition and the medical statuses associated with the group of persons with regard to the medical condition based on the results of analyzing the temporal medical data (e.g., clinical profile data) associated with the group of persons and the domain knowledge data relating to the medical condition, such as more fully described herein. The ontology can comprise a group of nodes, wherein respective nodes of the group of nodes can correspond to respective medical statuses associated with persons (e.g., patients or subjects) with regard to the medical condition (e.g., a disease or other medical condition). The ontology developer component can arrange, order, and/or rank the respective nodes based on the respective levels of stringency, severity, and/or progression associated with the respective medical statuses (e.g., Single status, SinglePersistent status, Multiple status, Multiple@SameVisit status, MultiplePersistentOR status, MultiplePersistentAND, and/or another type of medical status), as such respective levels of stringency, severity, and/or progression associated with the respective medical statuses can be determined based on the domain knowledge data relating to the medical condition.

At 704, based on the ontology, at a defined time, a group of global temporal features relating to a person and a level of severity associated with the medical condition can be determined, wherein the group of global temporal features can facilitate a prediction of a future medical status relating to the medical condition and associated with the person. At the defined time (e.g., index or prediction time), based on the ontology and medical data relating to the person (e.g., medical data regarding lab test results, biomarkers, commodities, or medications associated with the person), the ontology generator component (e.g., employing the feature extractor component) can determine or identify the group of global temporal features relating to the person (e.g., patient) and the level of severity and/or level of progression associated with the medical condition, and can extract the group of global temporal features from the ontology. The group of global temporal features can facilitate the prediction of the future medical status relating to the medical condition and associated with the person. For instance, the group of global temporal features and/or other desired features (e.g., other dynamic features and/or basic features) can be applied to a prediction model, and, based on the application of such features to the prediction model, the prediction model can predict the future medical status relating to the medical condition and associated with the person. For example, the prediction model can predict the risk that the person will develop the medical condition at a certain time(s) or predict the time of the onset of the medical condition in the person, if the person has not yet developed the medical condition, or can predict the progression of the medical condition in the person over time, if the person already has been diagnosed with the medical condition.

Figure 8:
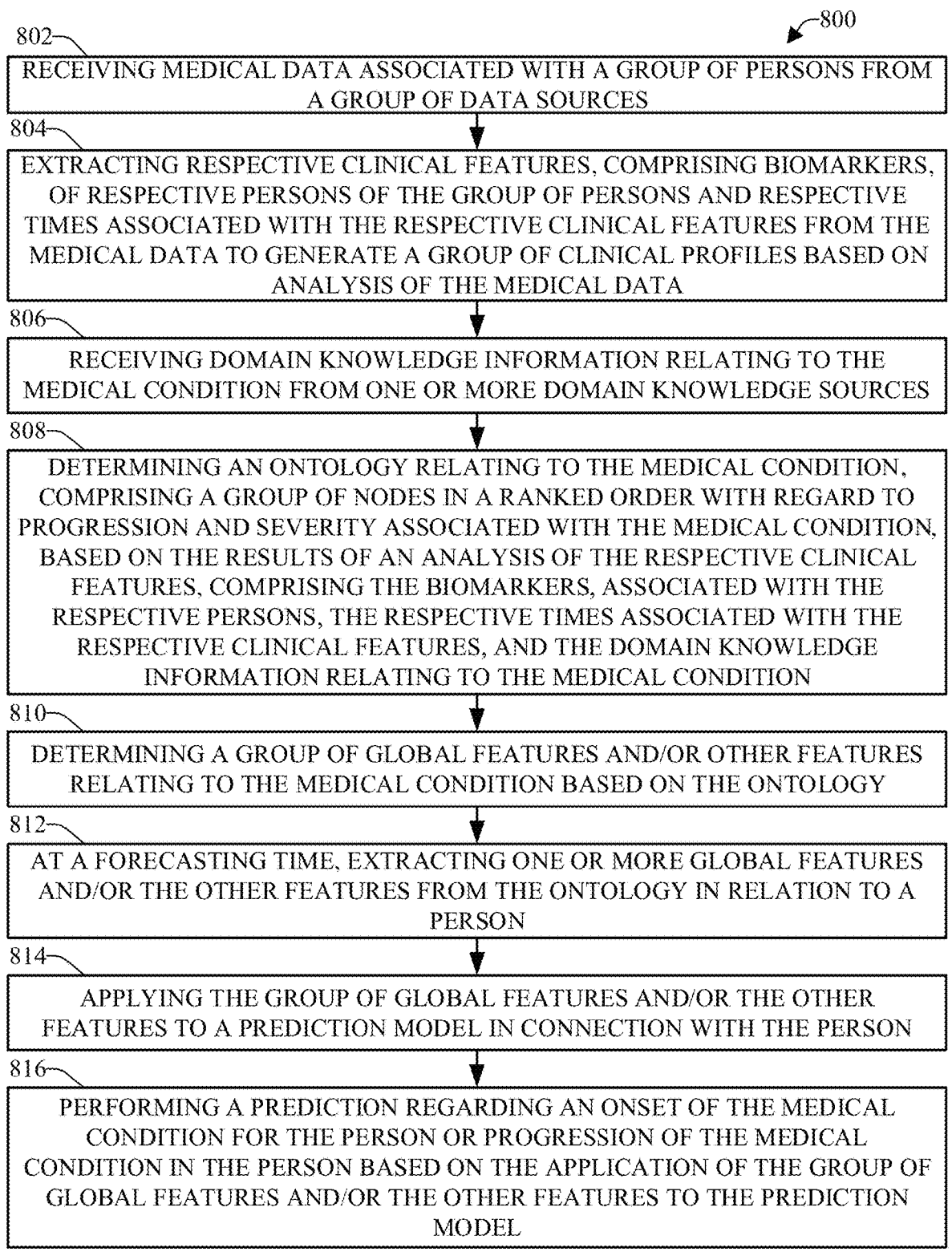
FIG. 8 depicts a flow diagram of another example, non-limiting method that can determine an ontology based on clinical features, comprising biomarkers, associated with persons to facilitate enhancing clinical predictions relating to a medical condition, in accordance with various aspects and embodiments of the disclosed subject matter.

FIG. 8 depicts a flow diagram of another example, non-limiting method 800 that can determine an ontology based on clinical features, comprising biomarkers, associated with persons (e.g., patients) to facilitate enhancing clinical predictions relating to a medical condition, in accordance with various aspects and embodiments of the disclosed subject matter. The method 800 can be performed by, for example, a system comprising or operatively coupled to an ontology generator component, a predictor component, and/or a processor component. Repetitive description of like elements employed in other embodiments described herein is or may be omitted for sake of brevity.

At 802, medical data associated with a group of persons can be received from a group of data sources. The ontology generator component can receive the medical data (e.g., temporal medical data) associated with the group of persons (e.g., patients) from one or more data sources (e.g., data source that can provide electronic health records associated with patients, data source such as a disease registry, or other desired data source).

At 804, respective clinical features, comprising biomarkers, of respective persons of the group of persons and respective times associated with the respective clinical features can be extracted from the medical data to generate a group of clinical profiles associated with the group of persons based on analysis of the medical data. The ontology generator component (e.g., employing the feature extractor component) can analyze the medical data associated with the group of persons. Based at least in part on the results of such analysis, the ontology generator component can extract, from the medical, the respective clinical features (e.g., lab test results, biomarker status, commodities, medications, or other clinical features) of the respective persons and the respective times associated with the respective clinical features from the medical data. The ontology generator component can generate respective clinical profiles associated with (e.g., for) respective persons of the group of persons based on the respective clinical features extracted from the medical data. A clinical profile associated with a person can comprise information regarding lab test results, biomarker information relating to a group of biomarkers associated with a medical condition, health or medical information associated with commodities (e.g., sensors or other medical devices) and relating to the medical condition, medications relating to the medical condition, or other clinical information relating to the medical condition.

At 806, domain knowledge information relating to the medical condition can be received from one or more domain knowledge sources. The ontology generator component can receive the domain knowledge information relating to the medical condition from one or more domain knowledge sources, which can comprise one or more medical experts who have expert knowledge regarding the medical condition or one or more domain knowledge databases that contain expert domain knowledge information relating to the medical condition that has been obtained from one or more medical experts who have expert knowledge regarding the medical condition.

At 808, an ontology relating to the medical condition, comprising a group of nodes in a ranked order with regard to progression and severity associated with the medical condition, can be determined based on the results of an analysis of the respective clinical features, comprising the biomarkers, associated with the respective persons, the respective times associated with the respective clinical features, and the domain knowledge information relating to the medical condition. The ontology generator component can analyze the clinical feature data associated with the respective clinical features of the respective persons and the respective times associated with the respective clinical features, and the domain knowledge information (e.g., expert domain knowledge) relating to the medical condition. Based on such analysis results, the ontology generator component can determine and generate the ontology relating to the medical condition. As part of the analysis and the determining of the ontology, the ontology generator component can determine respective nodes of the group of nodes where the respective nodes can relate to respective levels of progression and/or severity associated with the medical condition, and can rank the respective nodes in order of the respective levels of progression and/or severity associated with the medical condition. The ontology generator component can structure and rank respective nodes of the ontology in order of the respective levels of progression and/or severity associated with the medical condition from a lowest level of progression and/or severity associated with the medical condition to a highest level of progression and/or severity associated with the medical condition, such as more fully described herein.

At 810, a group of global features and/or other features relating to the medical condition can be determined based on the ontology. From the ontology, the ontology generator component can determine and/or develop the group of global features (e.g., global temporal features), comprising one or more global features, relating to the medical condition based at least in part on the ontology. For example, from the ontology, the ontology generator component can determine and/or develop global features, such as highest risk so far (HighestRiskSoFar) and pathway length to the highest risk so far (PathwayLengthToHighestRiskSoFar), relating to the medical condition (e.g., type 1 diabetes or other type of medical condition), such as more fully described herein. In some embodiments, in addition to the global features, the ontology generator component can determine, develop, and/or extract one or more other features (e.g., dynamic biomarkers (biomarker_dyn), biomarker counts (Biomarker-Counts), or other feature) relating to the medical condition based on the ontology and/or information obtained from another data source(s).

At 812, at a forecasting time, one or more global features and/or the other features can be extracted from the ontology in relation to a person (e.g., patient). At 814, the group of global features and/or the other features can be applied to a prediction model in connection with the person. At 816, a prediction regarding an onset of the medical condition for the person or progression of the medical condition in the person can be performed based on the application of the group of global features and/or the other features to the prediction model. At a desired forecasting time (e.g., index time or prediction time), the ontology generator component can extract the one or more global features and/or the other features from the ontology (and/or another data source) in relation to the person (e.g., patient) based on analysis of the ontology and/or clinical features (e.g., lab results, biomarkers, commodities, medications, or other clinical features) relating to the person, as more fully described herein. The ontology generator component can apply or input the one or more global features and/or the other features to the prediction model (of the predictor component) and/or train the prediction model based on the one or more global features and/or the other features. Based on the application of the one or more global features and/or the other features to the prediction model, the prediction model (of the predictor component) can predict the onset of the medical condition for the person, if the person does not yet have the medical condition, or can predict the progression of the medical condition in the person, if the person already has the medical condition, as more fully described herein.

For simplicity of explanation, the methods and/or computer-implemented methods are depicted and described as a series of acts. It is to be understood and appreciated that the disclosed subject matter is not limited by the acts illustrated and/or by the order of acts, for example acts can occur in various orders and/or concurrently, and with other acts not presented and described herein. Furthermore, not all illustrated acts can be required to implement the computer-implemented methods in accordance with the disclosed subject matter. In addition, those skilled in the art will understand and appreciate that the computer-implemented methods could alternatively be represented as a series of interrelated states via a state diagram or events. Additionally, it should be further appreciated that the computer-implemented methods disclosed hereinafter and throughout this specification are capable of being stored on an article of manufacture to facilitate transporting and transferring such computer-implemented methods to computers. The term article of manufacture, as used herein, is intended to encompass a computer program accessible from any computer-readable device or storage media.

Figure 9:
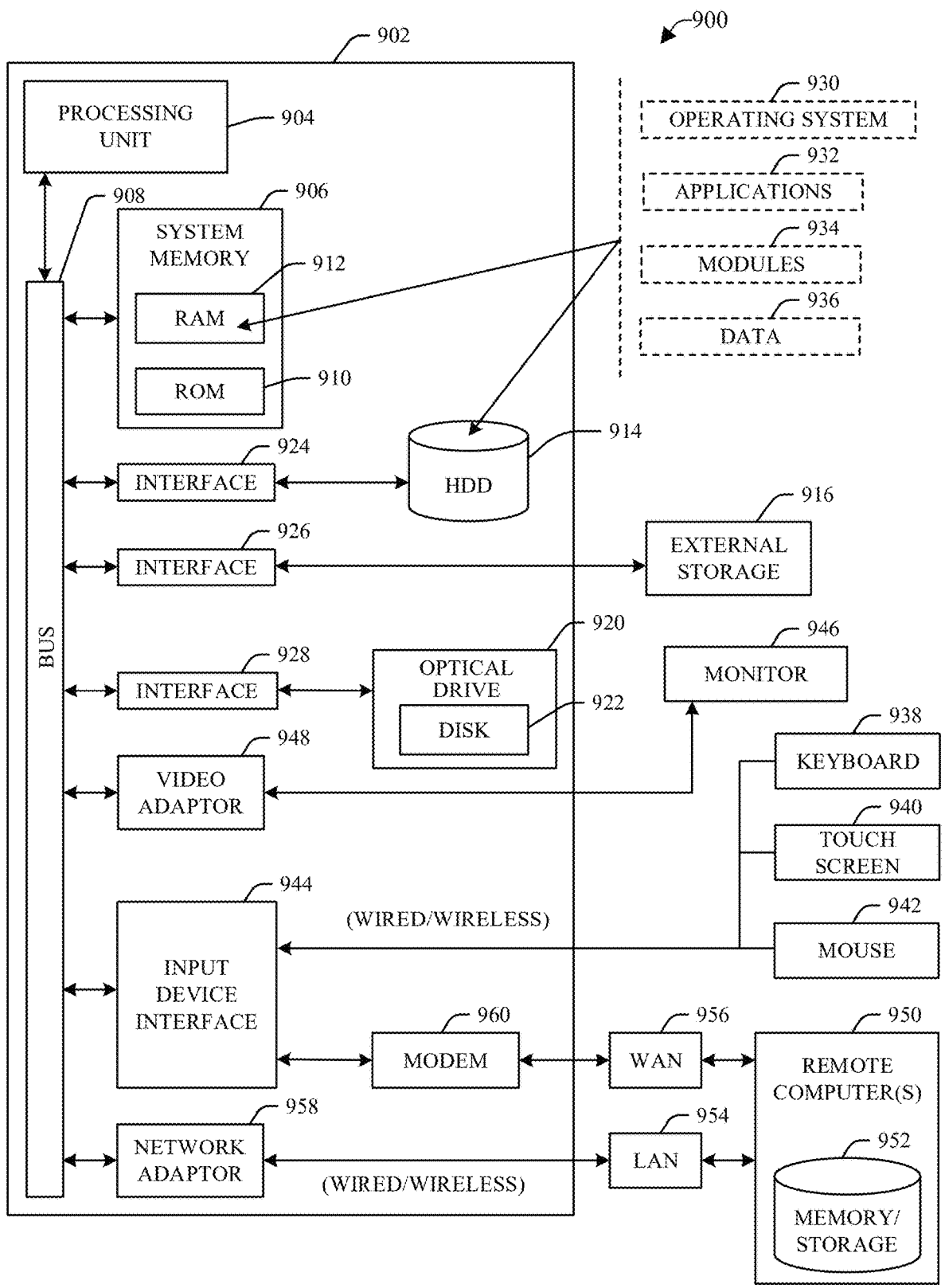
FIG. 9 illustrates a block diagram of an example, non-limiting operating environment in which one or more embodiments described herein can be facilitated.

In order to provide additional context for various embodiments described herein, FIG. 9 and the following discussion are intended to provide a general description of a suitable computing environment 900 in which the various embodiments of the embodiments described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the methods can be practiced with other computer system configurations, including single-processor or multiprocessor computer systems, minicomputers, mainframe computers, Internet of Things (IoT) devices, distributed computing systems, as well as desktop computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 9, the example environment 900 for implementing various embodiments of the aspects described herein includes a computer 902, the computer 902 including a processing unit 904, a system memory 906 and a system bus 908. The system bus 908 couples system components including, but not limited to, the system memory 906 to the processing unit 904. The processing unit 904 can be any of various commercially available processors. Dual microprocessors and other multi-processor architectures can also be employed as the processing unit 904.

The system bus 908 can be any of several types of bus structure that can further interconnect to a memory bus (with or without a memory controller), a peripheral bus, and a local bus using any of a variety of commercially available bus architectures. The system memory 906 includes ROM 910 and RAM 912. A basic input/output system (BIOS) can be stored in a non-volatile memory such as ROM, erasable programmable read only memory (EPROM), EEPROM, which BIOS contains the basic routines that help to transfer information between elements within the computer 902, such as during startup. The RAM 912 can also include a high-speed RAM such as static RAM for caching data.

The computer 902 further includes an internal hard disk drive (HDD) 914 (e.g., EIDE, SATA), one or more external storage devices 916 (e.g., a magnetic floppy disk drive (FDD) 916, a memory stick or flash drive reader, a memory card reader, etc.) and an optical disk drive 920 (e.g., which can read or write from a CD-ROM disc, a DVD, a BD, etc.). While the internal HDD 914 is illustrated as located within the computer 902, the internal HDD 914 can also be configured for external use in a suitable chassis (not shown). Additionally, while not shown in environment 900, a solid state drive (SSD) could be used in addition to, or in place of, an HDD 914. The HDD 914, external storage device(s) 916 and optical disk drive 920 can be connected to the system bus 908 by an HDD interface 924, an external storage interface 926 and an optical drive interface 928, respectively. The interface 924 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 902, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 912, including an operating system 930, one or more application programs 932, other program modules 934 and program data 936. All or portions of the operating system, applications, modules, and/or data can also be cached in the RAM 912. The systems and methods described herein can be implemented utilizing various commercially available operating systems or combinations of operating systems.

Computer 902 can optionally comprise emulation technologies. For example, a hypervisor (not shown) or other intermediary can emulate a hardware environment for operating system 930, and the emulated hardware can optionally be different from the hardware illustrated in FIG. 9. In such an embodiment, operating system 930 can comprise one virtual machine (VM) of multiple VMs hosted at computer 902. Furthermore, operating system 930 can provide runtime environments, such as the Java runtime environment or the .NET framework, for applications 932. Runtime environments are consistent execution environments that allow applications 932 to run on any operating system that includes the runtime environment. Similarly, operating system 930 can support containers, and applications 932 can be in the form of containers, which are lightweight, standalone, executable packages of software that include, e.g., code, runtime, system tools, system libraries and settings for an application.

Further, computer 902 can be enable with a security module, such as a trusted processing module (TPM). For instance with a TPM, boot components hash next in time boot components, and wait for a match of results to secured values, before loading a next boot component. This process can take place at any layer in the code execution stack of computer 902, e.g., applied at the application execution level or at the operating system (OS) kernel level, thereby enabling security at any level of code execution.

A user can enter commands and information into the computer 902 through one or more wired/wireless input devices, e.g., a keyboard 938, a touch screen 940, and a pointing device, such as a mouse 942. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 904 through an input device interface 944 that can be coupled to the system bus 908, but can be connected by other interfaces, such as a parallel port, an IEEE 1394 serial port, a game port, a USB port, an IR interface, a BLUETOOTH® interface, etc.

A monitor 946 or other type of display device can be also connected to the system bus 908 via an interface, such as a video adapter 948. In addition to the monitor 946, a computer typically includes other peripheral output devices (not shown), such as speakers, printers, etc.

The computer 902 can operate in a networked environment using logical connections via wired and/or wireless communications to one or more remote computers, such as a remote computer(s) 950. The remote computer(s) 950 can be a workstation, a server computer, a router, a desktop computer, portable computer, microprocessor-based entertainment appliance, a peer device or other common network node, and typically includes many or all of the elements described relative to the computer 902, although, for purposes of brevity, only a memory/storage device 952 is illustrated. The logical connections depicted include wired/wireless connectivity to a local area network (LAN) 954 and/or larger networks, e.g., a wide area network (WAN) 956. Such LAN and WAN networking environments are commonplace in offices and companies, and facilitate enterprise-wide computer networks, such as intranets, all of which can connect to a global communications network, e.g., the Internet.

When used in a LAN networking environment, the computer 902 can be connected to the local network 954 through a wired and/or wireless communication network interface or adapter 958. The adapter 958 can facilitate wired or wireless communication to the LAN 954, which can also include a wireless access point (AP) disposed thereon for communicating with the adapter 958 in a wireless mode.

When used in a WAN networking environment, the computer 902 can include a modem 960 or can be connected to a communications server on the WAN 956 via other means for establishing communications over the WAN 956, such as by way of the Internet. The modem 960, which can be internal or external and a wired or wireless device, can be connected to the system bus 908 via the input device interface 944. In a networked environment, program modules depicted relative to the computer 902 or portions thereof, can be stored in the remote memory/storage device 952. It will be appreciated that the network connections shown are example and other means of establishing a communications link between the computers can be used.

When used in either a LAN or WAN networking environment, the computer 902 can access cloud storage systems or other network-based storage systems in addition to, or in place of, external storage devices 916 as described above. Generally, a connection between the computer 902 and a cloud storage system can be established over a LAN 954 or WAN 956, e.g., by the adapter 958 or modem 960, respectively. Upon connecting the computer 902 to an associated cloud storage system, the external storage interface 926 can, with the aid of the adapter 958 and/or modem 960, manage storage provided by the cloud storage system as it would other types of external storage. For instance, the external storage interface 926 can be configured to provide access to cloud storage sources as if those sources were physically connected to the computer 902.

The computer 902 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Wi-Fi, or Wireless Fidelity, allows connection to the Internet from a couch at home, in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

One or more embodiments can be a system, a method, an apparatus and/or a computer program product at any possible technical detail level of integration. The computer program product can include a computer readable storage medium (or media) having computer readable program instructions thereon for causing a processor to carry out aspects of the one or more embodiments. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can include the following: a portable computer diskette, a hard disk, a RAM, a ROM, an erasable programmable read-only memory (EPROM or Flash memory), a SRAM, a portable CD-ROM, a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the disclosed subject matter can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the disclosed subject matter.

Aspects of disclosed subject matter are described herein with reference to flowchart illustrations and/or block diagrams of methods, apparatus (systems), and computer programs products according to embodiments of the subject disclosure. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create method for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the disclosed subject matter. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can be implemented in combination with other program modules. Generally, program modules include routines, programs, components, data structures, etc. that perform particular tasks and/or implement particular abstract data types. Moreover, those skilled in the art will appreciate that the computer-implemented methods disclosed herein can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other method to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include ROM, PROM, EPROM, EEPROM, flash memory, or nonvolatile RAM (e.g., FeRAM). Volatile memory can include RAM, which can act as external cache memory, for example. By way of illustration and not limitation, RAM is available in many forms such as SRAM, DRAM, SDRAM, DDR SDRAM, ESDRAM, SLDRAM, DRRAM, DRDRAM, and RDRAM. Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
   determining, by a system comprising a processor, an ontology relating to a medical condition and medical statuses associated with a group of persons with regard to the medical condition based on analyzing temporal medical data associated with the group of persons and domain knowledge data relating to the medical condition;
   training, by the system, using the ontology, a prediction model comprising a survival model that comprises a first objective function and a second objective function, to predict at least one of onset of the medical condition or progression of the medical condition in persons, wherein the first objective function is associated with relative risks of persons being diagnosed with the onset of the medical condition, and the second objective function is associated with predicting actual times of persons being diagnosed with the onset of the medical condition;
   based on the ontology, at a defined time, determining, by the system, a group of global temporal features relating to a person and a level of severity associated with the medical condition that facilitates predicting the at least one of the onset or the progression of the medical condition in the person;

training, by the system, the prediction model to determine respective weights of the group of global temporal features to apply in predicting the at least one of the onset or the progression of the medical condition in the person, wherein the training comprises simultaneously optimizing the first objective function and the second objective function; and generating, by the system, via the prediction model, using the group of global temporal features, a prediction regarding the at least one of the onset of the medical condition or the progression of the medical condition in the person.

2. The computer-implemented method of claim 1, wherein the determining of the group of global temporal features comprises:

at the defined time, determining the group of global temporal features relating to the person, based on the ontology and a defined-time medical status associated with the person at the defined time, wherein the group of global temporal features relate to the level of severity or a level of progression associated with the medical condition.

3. The computer-implemented method of claim 1, further comprising:

receiving, by the system, the domain knowledge data relating to the medical condition from a group of medical experts who satisfy a defined medical expert criterion or from a database in which the domain knowledge data is stored, wherein development of the domain knowledge data is based on knowledge of the group of medical experts with regard to the medical condition.

4. The computer-implemented method of claim 1, further comprising:

analyzing, by the system, the domain knowledge data relating to the medical condition and the temporal medical data associated with the group of persons; and based on the analyzing, determining, by the system, a number of nodes in a group of nodes of the ontology, one or more types of nodes for the group of nodes, or an arrangement of nodes of the group of nodes in the ontology, wherein the nodes relate to respective levels of severity or respective levels of progression with regard to the medical condition.

5. The computer-implemented method of claim 4, further comprising:

determining, by the system, a first number of, and one or more types of, biomarker positivity results associated with the person with regard to a clinical visit based on first temporal medical data obtained in connection with the clinical visit;

determining, by the system, a second number of, and the one or more types of, the biomarker positivity results associated with the person with regard to two consecutive clinical visits based on the first temporal medical data and second temporal medical data obtained in connection with the two consecutive clinical visits, comprising the clinical visit; and based on the determining of the first number of, and the one or more types of, the biomarker positivity results associated with the person with regard to the clinical visit, and based on the determining of the second number of, and the one or more types of, the biomarker positivity results associated with the person with regard to the two consecutive clinical visits, determining, by the system, a node relating to a medical status associated with the person in connection with the medical condition, wherein the ontology is determined based on the node.

6. The computer-implemented method of claim 4, wherein the group of nodes comprise a first node and a second node, and wherein the computer-implemented method further comprises:

determining, by the system, a first level of severity or a first level of progression associated with a first medical status with regard to the medical condition based on the analyzing of the domain knowledge data and the temporal medical data;

determining, by the system, a second level of severity or a second level of progression associated with a second medical status with regard to the medical condition based on the analyzing of the domain knowledge data and the temporal medical data, wherein the second level of severity or the second level of progression associated with the second medical status is determined to be higher than the first level of severity or the first level of progression associated with the first medical status; and ranking, by the system, the second node associated with the second medical status higher than the first node associated with the first medical status in the ontology based on the determining that the second level of severity or the second level of progression associated with the second medical status is higher than the first level of severity or the first level of progression associated with the first medical status.

7. The computer-implemented method of claim 1, further comprising:

receiving, by the system, electronic health records or electronic disease registry information associated with the group of persons;

extracting, by the system, the temporal medical data associated with the group of persons from the electronic health records or the electronic disease registry information, wherein respective portions of the temporal medical data are associated with respective time periods; and generating, by the system, clinical profiles associated with persons of the group of persons based on the temporal medical data, wherein the clinical profiles comprise testing results information relating to medical testing results associated with the persons, biomarker information relating to biomarkers associated with the persons, commodities information relating to commodities associated with the persons, medication information relating to medications associated with the persons, or time information indicating times associated with the medical testing results, the biomarkers, the commodities, or the medications.

8. The computer-implemented method of claim 7, wherein the temporal medical data comprises biomarker positivity results of medical tests performed at the respective time periods, wherein the medical tests relates to the medical statuses associated with the group of persons in connection with the medical condition.

9. The computer-implemented method of claim 1, further comprising:

at the defined time, extracting, by the system, the group of global temporal features from the ontology or one or more other medical condition-related features from the ontology or a data source, wherein the group of global temporal features are determined based on the ontology and a defined-time medical status associated with the person at the defined time.

10. The computer-implemented method of claim 9, wherein the group of global temporal features comprise a first global temporal feature relating to a highest risk to date that the person has satisfied up to the defined time associated with the predicting or a second global temporal feature relating to a pathway length to the highest risk to date that is defined as a length of a trajectory to the highest risk to date associated with the person.

11. The computer-implemented method of claim 9, wherein the one or more other medical condition-related features comprise a dynamic biomarker or cumulative biomarker counts up to the defined time associated with the prediction.

12. The computer-implemented method of claim 1, wherein the generating the prediction is further based on one or more other medical condition-related features from the ontology or a data source.

13. A system, comprising:
a memory that stores computer-executable components; and
a processor, operatively coupled to the memory, that executes the computer-executable components, the computer-executable components comprising:
an ontology generator component that:
generates an ontology relating to a disease and medical statuses associated with a group of patients in connection with the disease based on an analysis of temporal clinical data associated with the group of patients and domain knowledge data relating to the disease,
trains, using the ontology, a prediction model comprising a survival model that comprises a first objective function and a second objective function, to predict at least one of onset of the medical condition or progression of a medical condition in patients, wherein the first objective function is associated with relative risks of patients being diagnosed with the onset of the medical condition, and the second objective function is associated with predicting actual times of patients being diagnosed with the onset of the medical condition,
based on the ontology, at an index time, extracts a group of global temporal features relating to a patient and a severity level associated with the disease, wherein the group of global temporal features facilitates predicting the at least one of the onset or the progression of the medical condition in the patient, and
trains the prediction model to determine respective weights of the group of global temporal features to apply in predicting the at least one of the onset or the progression of the medical condition in the patient, wherein the training of the prediction model comprises simultaneously optimizing the first objective function and the second objective function; and
a prediction component that generates, via the prediction model, using the group of global temporal features, a prediction regarding the at least one of the onset of the medical condition or the progression of the medical condition in the patient.

14. The system of claim 13, wherein at the index time, the ontology generator component determines the group of global temporal features relating to the patient, based on the ontology and an index-time medical status associated with the patient at the index time, wherein the group of global temporal features relate the severity level or a progression level associated with the disease.

15. The system of claim 13, wherein the prediction component generates the prediction based further on one or more other medical condition-related features from the ontology or a data source.

16. The system of claim 13, wherein the ontology generator component analyzes the domain knowledge data relating to the disease and the temporal clinical data associated with the group of patients,
wherein, based on the analysis, the ontology generator component determines a number of nodes in a group of nodes of the ontology, one or more types of nodes for the group of nodes, or a ranking order of nodes of the group of nodes in the ontology, and
wherein the nodes relate to respective severity levels or respective progression levels with regard to the disease.

17. The system of claim 13, wherein the ontology generator component generates clinical profiles associated with patients of the group of patients based on the analysis of the temporal clinical data associated with the group of patients, wherein the clinical profiles comprise testing results data relating to medical testing results associated with the patients, biomarker data relating to biomarkers associated with the patients, commodities data relating to commodities associated with the patients, medication data relating to medications associated with the patients, or time data indicating times associated with the medical testing results, the biomarkers, the commodities, or the medications.

18. The system of claim 13, wherein the group of global temporal features comprise a first global temporal feature relating to a highest risk to date that the patient has attained up to the index time associated with the prediction or a second global temporal feature relating to a pathway length to the highest risk to date that is defined as a length of a trajectory to the highest risk to date associated with the patient.

19. A computer program product that facilitates determining an ontology, the computer program product comprising a computer readable storage medium having program instructions embodied therewith, the program instructions are executable by a processor to cause the processor to:
determine the ontology relating to a medical condition and medical statuses associated with a group of patients with regard to the medical condition based on analyzing temporal medical data associated with the group of patients and domain knowledge information relating to the medical condition;
train, using the ontology, a prediction model comprising a survival model that comprises a first objective function and a second objective function, to predict at least one of onset of the medical condition or progression of the medical condition in patients, wherein the first objective function is associated with relative risks of patients being diagnosed with the onset of the medical condition, and the second objective function is associated with predicting actual times of patients being diagnosed with the onset of the medical condition;
based on the ontology, at a prediction time, determine a group of global temporal features relating to a patient and a level of severity associated with the medical condition that facilitates predicting the at least one of the onset or the progression of the medical condition in the patient train the prediction model to determine respective weights of the group of global temporal features to apply in predicting the at least one of the onset or the progression of the medical condition in the patient, wherein the training of the prediction model comprises simultaneously optimizing the first objective function and the second objective function; and generate, via the prediction model, using the group of global temporal features, a prediction regarding the at least one of the onset of the medical condition or the progression of the medical condition in the patient.

20. The computer program product of claim 19, wherein the program instructions are executable by the processor to cause the processor to:

at the prediction time, determine the group of global temporal features relating to the patient, based on the ontology and a prediction-time medical status associated with the patient, wherein the group of global temporal features relate to the level of severity or a level of progression associated with the medical condition; and extract the group of global temporal features from the ontology.

\* \* \* \* \*